United States Patent
Wakao et al.

(10) Patent No.: US 10,156,577 B2
(45) Date of Patent: Dec. 18, 2018

(54) METHOD FOR DIAGNOSING FIBROMYALGIA SYNDROME, AND KIT THEREFOR

(71) Applicants: NATIONAL UNIVERSITY CORPORATION HOKKAIDO UNIVERSITY, Sapporo-shi (JP); MIRACA RESEARCH INSTITUTE G.K., Hachioji (JP)

(72) Inventors: Hiroshi Wakao, Hokkaido (JP); Chie Sugimoto, Hokkaido (JP)

(73) Assignees: NATIONAL UNIVERSITY CORPORATION HOKKAIDO UNIVERSITY, Sapporo (JP); MIRACA RESEARCH INSTITUTE G.K., Hachioji (JP)

( * ) Notice: Subject to any disclaimer, the term of this patent is extended or adjusted under 35 U.S.C. 154(b) by 13 days.

(21) Appl. No.: 15/079,503

(22) Filed: Mar. 24, 2016

(65) Prior Publication Data
US 2017/0097364 A1 Apr. 6, 2017

(30) Foreign Application Priority Data
Oct. 1, 2015 (JP) ................................. 2015-196050

(51) Int. Cl.
*G01N 33/68* (2006.01)
*G01N 33/569* (2006.01)

(52) U.S. Cl.
CPC ... *G01N 33/6896* (2013.01); *G01N 33/56972* (2013.01); *G01N 33/6863* (2013.01); *G01N 33/6872* (2013.01); *G01N 2333/70514* (2013.01); *G01N 2333/70517* (2013.01); *G01N 2333/70596* (2013.01); *G01N 2333/7158* (2013.01); *G01N 2800/2842* (2013.01)

(58) Field of Classification Search
None
See application file for complete search history.

(56) References Cited

U.S. PATENT DOCUMENTS

2011/0160434 A1 6/2011 Nishioka et al.
2013/0196980 A1 8/2013 Yamano et al.

FOREIGN PATENT DOCUMENTS

| WO | WO 97/14963 A1 | 4/1997 |
|---|---|---|
| WO | WO 2010/004962 A1 | 1/2010 |
| WO | WO 2012/046708 A1 | 4/2012 |

OTHER PUBLICATIONS

Wakao et al., Cell Stem Cell, 2013; 12, 546-558. (Year: 2013).*
Willing et al., Eur. J. Immunol. 2014. 44: 3119-3128. (Year: 2014).*
Tanaka et al., Arch Virol., 2002; 147: 195-203. (Year: 2002).*
Sugimoto et al., PLOS ONE, Apr. 8, 2015: DOI:10.1371/journal.pone.0121124; 18 pages total. (Year: 2015).*

* cited by examiner

*Primary Examiner* — Christina M Borgeest
(74) *Attorney, Agent, or Firm* — Oblon, McClelland, Maier & Neustadt, L.L.P.

(57) ABSTRACT

The present invention provides a novel marker for diagnosing fibromyalgia syndrome (FMS). More specifically, the present invention provides a method for diagnosing FMS, comprising measurement of (1) the relative frequency of MAITs to the total T cells in a sample; or (2) the expression level of one or more surface antigens selected from the group consisting of CD4, CD8, CCR4, CCR7, CXCR1, NKp80, CD150, CD107a, CD8β, CD44 and CXCR4 for MAITs in a sample, wherein the sample is a biological sample collected from a human; and a diagnosis kit for FMS, comprising a means for measuring (1) the relative frequency of MAITs to the total T cells in a sample; or (2) the expression level of one or more surface antigens selected from the group consisting of CD4, CD8, CCR4, CCR7, CXCR1, NKp80, CD150, CD107a, CD8β, CD44 and CXCR4 for MAITs in a sample, wherein the sample is a biological sample collected from a human.

13 Claims, 28 Drawing Sheets

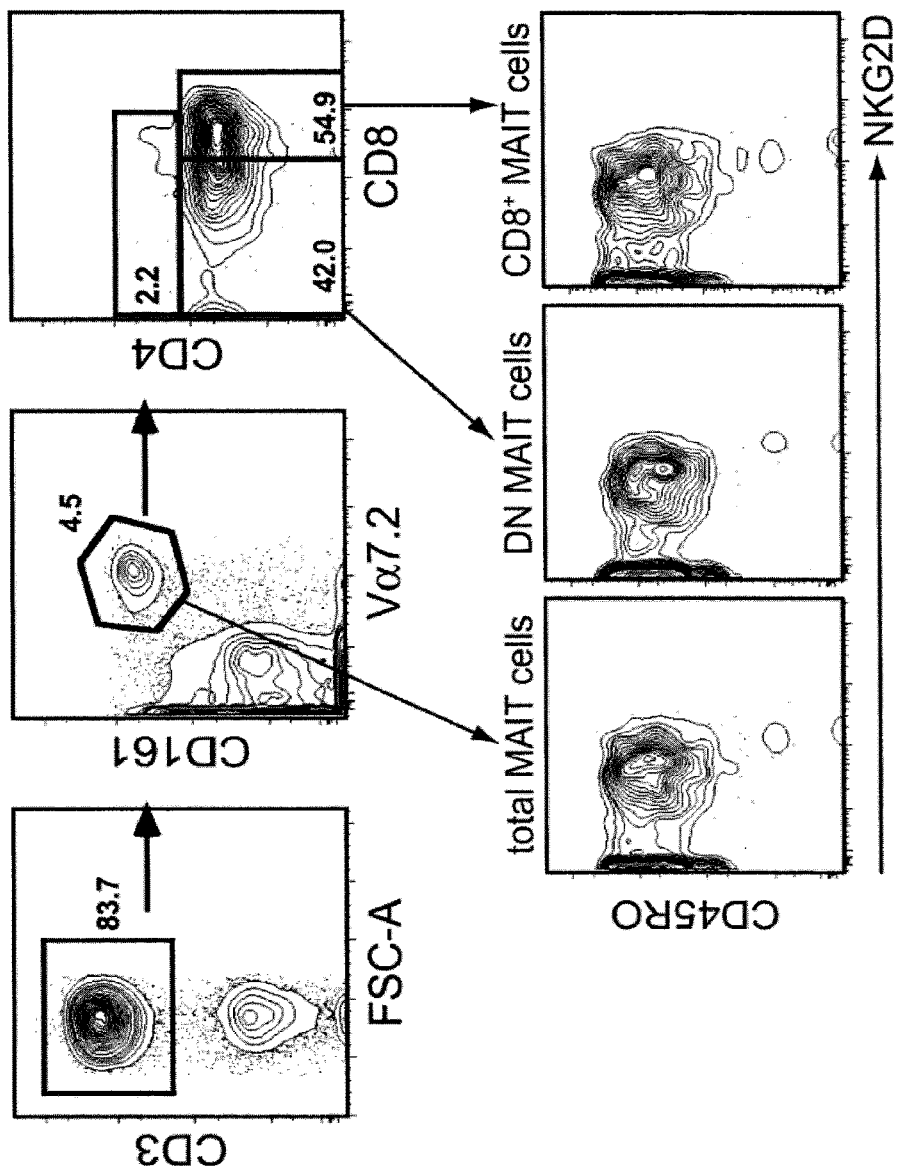

METHOD FOR DIAGNOSING FIBROMYALGIA SYNDROME, AND KIT THEREFOR

TECHNICAL FIELD

The present invention relates to a method for diagnosing fibromyalgia syndrome, a kit therefor, etc. Especially, the present invention relates to a method for differentiating a fibromyalgia syndrome patient from a healthy subject, a method for differentiating a fibromyalgia syndrome patient from those of similar painful diseases (e.g., spondyloarthritis, rheumatoid arthritis), and a method for evaluating a pain level of a fibromyalgia syndrome patient, and a kit therefor.

BACKGROUND ART

Fibromyalgia syndrome (FMS) is an intractable disease of unknown cause, characterized by the symptoms such as chronic systemic pain, fatigue and sleep disorder. Morbidity of FMS is very high in women, and the estimated number of patients in Japan is about 2 millions (~3% of the population are affected in USA according to the American Fibromyalgia Association). However, diagnosis of FMS is extremely difficult, and sometimes it takes 5 to 10 years for the patient to be suspected and finally diagnosed as FMS. FMS is fundamentally different from other intractable diseases because no anomaly is found in the clinical parameters currently used in many hospitals. As a result, FMS patients are often diagnosed as having mental disorders. Moreover, since many physicians do not regard FMS as a disease, FMS patients suffer from the disease physically and mentally. Aggravation of FMS can be prevented by an appropriate treatment at an early stage of pathogenesis. However, the symptom will aggravate if the patient fails to receive an appropriate treatment at early stage. Thereafter, FMS patients will suffer intolerable pain, fatigue and eventually have a difficulty even in daily life.

Sound diagnosis of FMS is more difficult due in part to the confusion with other diseases that exhibit similar symptoms. For example, systemic pain is not a symptom specific for FMS, but it also occurs in other diseases such as rheumatoid arthritis (RA) and spondyloarthritis (SpA). Further, FMS patients often suffer from SpA and/or RA simultaneously. Accordingly, differential diagnosis of FMS is difficult even for a specialist of RA or of the pain clinicians. A current method for diagnosing FMS is a tender point test. However, because it relies on the pain at the tender points, it is not objective, rather subjective in nature. Thus, there has been a demand for an advent of method(s) to differentiate FMS from other pain-provoking diseases promptly, accurately and objectively.

Regarding determination of FMS, some technics using a molecular marker or the like are known (see WO1997/014963, WO2012/046708, and WO2010/004962).

SUMMARY OF INVENTION

Problem to be Solved by the Invention

An object of the present invention is to provide a novel marker useful for diagnosing FMS.

Means for Solving Problem

As a result of extensive studies, the inventors have found that several cell surface antigens in mucosal-associated invariant T cells (MAITs) are useful markers for diagnosing FMS, thereby completing the present invention.

The present invention comprises the followings:

[1] A method for diagnosing FMS by measuring (1) the relative frequency of MAITs to the total T cells in a sample, or (2) the expression level of one or more surface antigens selected from the group consisting of CD4, CD8, CCR4, CCR7, CXCR1, NKp80, CD150, CD107a, CD8β, CD44 and CXCR4 for MAITs in a sample, wherein said sample is a biological sample collected from a human.

[2] The method according to [1], wherein the method is for differentiating FMS, SpA, and/or RA from healthy subjects.

[3] The method according to [2], wherein said surface antigens are selected from the group consisting of CD4, CCR4, CCR7, CSCR1, NKp80, CD150, CD107a and CD8β.

[4] The method according to [2], wherein the expression level of one or more surface antigens selected from the group consisting of CCR7, NKp80, CD150 and CD8β for CD8 positive (CD8$^+$) cells in said MAITs is measured.

[5] The method according to [2], wherein the expression level of one or more surface antigens selected from the group consisting of CCR4, CXCR1 and CD107a for CD4 and CD8 double negative (CD4$^-$CD8$^-$) cells in said MAITs is measured.

[6] The method according to [2], wherein said surface antigen is CD44 or CXCR1 or both CD44 and CXCR1.

[7] The method according to [2], wherein the expression level of CXCR1 for the CD4$^-$CD8$^-$ cells in said MAITs is measured.

[8] The method according to [2], wherein the surface antigen is CXCR4.

[9] The method according to [1], wherein said method is the following (a) or (b):
(a) a method for determining the pain level of a FMS patient, comprising measurement of the relative frequency of MAITs to the total T cells; or
(b) a method for differentiating a FMS patient from a healthy subject, comprising measurement of the relative frequency of CD4$^+$ MAITs to the total T cells.

[10] The method according to any one of [1] to [9], wherein the sample is a peripheral blood.

[11] The method according to any one of [1] to [10], wherein the expression level is a protein amount.

[12] The method according to [11], wherein the protein level is measured by using an antibody against the antigens.

[13] A diagnosis kit for FMS, comprising a means for measuring (1) the relative frequency of MAITs to the total T cells in a sample; or (2) the expression level of one or more surface antigens selected from the group consisting of CD4, CD8, CCR4, CCR7, CXCR1, NKp80, CD150, CD107a, CD8β, CD44 and CXCR4 for MAITs in a sample, wherein said sample is a biological sample collected from a human.

[14] A diagnosis kit according to [13], wherein said means is an antibody.

SIGNIFICANCE OF THE INVENTION

The method and the kit of the present invention are useful for the diagnosis of FMS.

BRIEF DESCRIPTION OF DRAWINGS

FIG. 1A shows representative fluorescence-activated cell sorting (FACS) profile of mucosal-associated invariant T cells (MAITs) and NKG2D expression in total, CD8$^+$, and CD4 and CD8-double negative (DN) MAITs in peripheral blood mononuclear cells (PBMC) from a FMS patient. The number in the figure shows the percentage of the indicated cell populations. MAITs are defined as Vα7.2-positive (Vα7.2$^+$) and CD161-highly positive (CD161$^{high}$) within CD3-positive (CD3$^+$) cells.

EMBODIMENTS FOR CARRYING OUT THE INVENTION

Figure 1B:
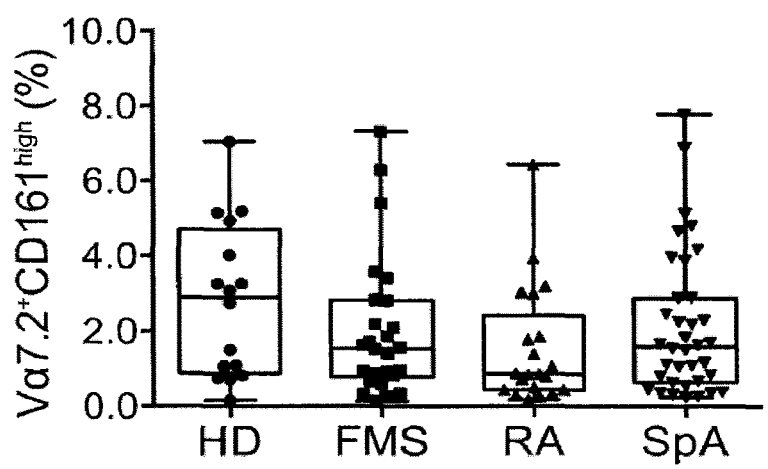
FIG. 1B shows the frequency of total MAITs in healthy subject (HD) (n=16), fibromyalgia syndrome (FMS) (n=26), rheumatoid arthritis (RA) (n=21), and spondyloarthritis (SpA) (n=36, missing one sample). The percentage of MAITs (Vα7.2$^+$CD161$^{high}$) within the total T cells (CD3$^+$) is shown. All data are presented as median (the same applies to FIG. 1C-H). Horizontal line: Median; boxes: 25th percentile and 75th percentile; whiskers: Minimum and Maximum (the same applies to FIG. 1C-H). Asterisk shows the group-pair exhibiting significance (the same applies to FIG. 1C-H). *: P<0.05, **: P<0.01 (P value adjusted with the Dunn's multicomponent test after the Kruskal-Wallis test) (the same applies to FIG. 1C-H).
Figure 1C:
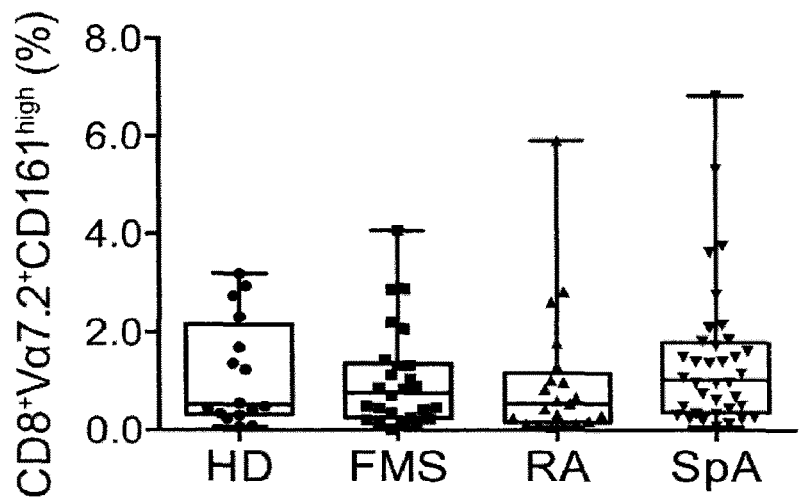
FIG. 1C shows the frequency of CD8$^+$ MAITs in HD, FMS, RA, and SpA. The percentage of CD8$^+$ MAITs (Vα7.2$^+$CD161$^{high}$CD8$^+$) within the total T cells (CD3$^+$) is shown.

The present invention provides a method for diagnosing FMS, comprising measurement of (1) the relative frequency of MAITs to the total T cells in a sample, or (2) the expression level of one or more surface antigens selected from the group consisting of CD4, CD8, CCR4, CCR7, CXCR1, NKp80, CD150, CD107a, CD8β, CD44 and CXCR4 for MAITs in a sample, wherein said sample is a biological sample collected from a human.

FMS can be classified into two, the first one is, primary FMS and the second one is secondary FMS. The primary FMS is caused by a mental factor, Complex Regional Pain Syndrome (CRPS) resulting from a surgery, an accident or the like, or chronic fatigue syndrome, and it is characterized that there is no basic disease that causes pain. On the contrary, the secondary FMS harbors a basic disease that causes pain (e.g. rheumatic disease, systemic lupus erythematosus, Sjogren's syndrome, spondyloarthritis ankylopoietica, hypothyroidism). The method of the present invention is useful especially for determining the primary FMS, but not limited thereto.

MAITs are an innate type T cell involved in an immune reaction. MAITs express invariant TCR. Specifically, TCRα chain on a human MAIT cells is consisted of Vα7.2-Jα33 (Le Bourhis et al. (2011), Trends in Immunol. 32, 212-218). In addition to invariant TCRα, MAITs expresses Natural killer (NK) antigens like CD161 (also called NKRP1) and an IL-18 receptor alpha chain (Cosmi et al. (2008), J. Exp. Med. 205, 1903-1916; and Bourhis et al. (2011), Trends in Immunol. 32, 212-218). Thus, the human MAITs can be defined as cells expressing a typical T cell marker (e.g., CD3) and also an invariant TCRα chain (Vα7.2-Jα33) and CD161.

MAITs are quite abundant in human peripheral blood, intestinal lamina propria, and liver. For example, MAITs are believed to play an important role in mucosal immunity. The biological sample used in the present invention is not limited as far as it contains MAITs. Examples of the biological sample include a blood sample (e.g., a peripheral blood sample), a mucous sample (e.g., an oral mucosa sample, a pharyngeal mucosa sample, an intestinal mucosa sample), a biopsy sample (e.g. an intestinal tract sample, a liver sample). Preferably, the biological sample is a blood sample.

MAITs consist of $CD4^+$ cells, $CD8^+$ cells and CD4 and CD8-double negative (DN) cells ($CD4^-CD8^-$ cell). Thus, MAITs can be classified further into $CD4^+$ cells, $CD8^+$ cells and $CD4^-CD8^-$ DN cells using CD4 and CD8 as markers.

In one embodiment, the method of the present invention comprises measuring the relative frequency of MAITs to the total T cells in a biological sample collected from a human.

In a method of the present invention, the measurement set forth can be carried out by using a T cell marker (e.g., CD3) and MAIT cell markers (e.g., Vα7.2-Jα33, CD161), for example.

For example, the relative frequency of MAITs to the total T cells can be carried out by counting the number of total T cells by use of a T cell marker, then counting the number of MAITs by use of a MAIT cell marker, and finally evaluating the ratio of MAITs to the total T cells. Specifically, the measurement may be carried out with a fluorescence-activated cell sorting (FACS) using the T cell marker and the MAIT cell markers.

Alternatively, the relative frequency can be measured in terms of the gene and/or protein expression. The relative frequency of MAITs to the total T cells can be determined as a ratio (the amount of the MAIT cell marker/the amount of the T cell marker) in a biological sample. For example, such ratio is calculated by measuring an amount of mRNA for the markers or of marker proteins in a mRNA extract or a protein extract prepared from a biological sample. Alternatively, the relative ratio may be calculated by measuring the relative expression of the marker mRNA or proteins in the extract.

For example, the measurement of mRNA amount can be carried out by means of hybridization and/or gene amplification (e.g., a primer, a probe). Specifically, examples of the method of using the means for measuring a gene expression level include a gene amplification method and a hybridization method. Examples of the gene amplification method include a thermal cycler gene amplification method (e.g., PCR) and an isothermal gene amplification method (e.g., LAMP, ICAN). Reverse transcriptase may be used simultaneously in the gene amplification method. Examples of the hybridization method include a northern blotting method and a microarray method.

For example, measurement of the protein expression can be carried out using a means for measuring a protein amount (e.g., an antibody, an aptamer). Specifically, examples of the method of using a means for measuring protein include enzyme immunoassay (EIA) (e.g., direct competitive ELISA, indirect competitive ELISA, sandwich ELISA), radioactive immunoassay (RIA), fluorescent immunoassay (FIA), a magnetic particle method, immunochromatography, luminescence immunoassay, spin immunoassay, Western-blotting, and latex agglutination. For the antibody, any antibodies such as a polyclonal antibody, a monoclonal antibody, and a modified antibody (e.g., a single-chain antibody) may be used.

For example, it is possible to determine the pain level of a FMS patient by measuring the relative frequency of MAITs to the total T cells. As shown in the up-left figure of FIG. 4C (FMS vs PVAS), the lesser the relative frequency of MAITs to the total T cells is, the more severely FMS patients suffer the pain. Therefore, according to the method of the present invention, it can be determined that the pain may be relatively weak when the relative frequency of MAITs to the total T cells is not less than the reference value. To the contrary, the pain may be relatively strong when the relative frequency of MAITs to the total T cells is less than the reference value. A plurality of reference values may be established. For example, the pain level is relatively low when the relative frequency of the MAITs to the total T cells is not less than the first reference value; the pain level is moderate when the relative frequency of MAITs to the total T cells is less than the first reference value and not less than the second reference value; and the pain level is relatively high when the relative frequency of MAITs to the total T cells is less than the second reference value. Alternatively, the relative frequency of MAITs to the total T cells is inversely correlated with the pain level, thus it is possible to presume the pain level from the relative frequency of MAITs to the total T cells by using an inverse relative coefficient.

Further, it is possible to differentiate a FMS patient from a healthy subject by measuring the relative frequency of $CD4^+$ MAITs to the total T cells. As shown in FIGS. 3 and 4, it can be understood that the relative frequency of the $CD4^+$ MAITs to the total T cells in a FMS patient is significantly small in comparison with that in a healthy subject. Therefore, according to the method of the present invention, it can be determined that the subject may be healthy when the relative frequency of $CD4^+$ MAITs to the total T cells is not less than the reference value and that the subject may be suffering from FMS when the relative frequency of $CD4^+$ MAITs to the total T cells is less than the reference value. For the reference value, a cutoff value appropriately established for enabling differentiation of a FMS patient from a healthy subject can be used.

In another embodiment, the method of the present invention comprises measuring an expression level of one or more surface antigens selected from the group consisting of CD4, CD8, CCR4, CCR7, CXCR1, NKp80, CD150, CD107a, $CD8\beta$, CD44, and CXCR4 for MAITs in a biological sample collected from a human. As mentioned above, MAITs can be classified further into a $CD4^+$ cell, $CD8^+$ cell, and $CD4^-CD8^-$ cell.

For example, it is possible to isolate or separate MAITs from a biological sample collected from a human and then to carry out the measurement of the expression level of the surface antigen in the isolated or separated MAITs. Specifically, the measurement can be carried out sequentially by fluorescence-activated cell sorting (FACS) analysis using MAIT cell markers and the surface antigens.

Alternatively, it is possible to isolate or separate MAITs from a biological sample collected from a human and then to carry out the measurement of the expression level of the surface antigen in a MAIT cell extract prepared from the isolated or separated cells. Isolation and separation of the MAITs can be carried out by a well-known method. For example, MAITs can be isolated or separated by using an antibody to MAIT cell markers (e.g., $V\alpha7.2$-$J\alpha33$, CD161), a tetramer molecule prepared by loading a vitamin $B_2$ derivative or antagonists on a MR-1 molecule. MR1 is the molecule that controls differentiation and proliferation of MAITs (Rahimpour A et al., J. Exp. Med. 2015, June 29; 212(7): 1095-108. doi: 10. 1084/jem. 20142110), or any other means capable of recognizing MAITs. It is also possible to measure the expression level of the surface antigen in the MAIT cell extract by quantifying the mRNA for the surface antigens or of the proteins for the surface antigen. Such quantification can be carried out similarly to the aforementioned methods to assess the relative frequency of MAITs.

In a specific embodiment, the method of the present invention is a method for differentiating a FMS patient from a healthy subject. In this case, it is possible to differentiate the FMS patient from the healthy subject by measuring an expression level of one or more surface antigens selected from the group consisting of CD4, CD8, CCR4, CCR7, CXCR1, NKp80, CD150, CD107a and $CD8\beta$ (Table 6 and FIGS. 3A-J).

For example, regarding the total MAITs ($CD4^+$, $CD8^+$, and DN cells), the expression level of one or more surface antigens selected from the group consisting of CCR4, CCR7, CXCR1, NKp80, CD150 and $CD8\beta$ in a FMS patient increases or decreases significantly in comparison with those in a healthy subject. Therefore, according to the method of the present invention, it can be determined that the subject may be healthy when the expression level of the surface antigen is not less than the reference value or not more than the reference value and that the subject may be suffering from FMS when the expression level of the surface antigen is less than the reference value or more than the reference value.

Regarding $CD8^+$ MAITs, the expression level of one or more surface antigens selected from the group consisting of CCR7, NKp80, CD150 and $CD8\beta$ in a FMS patient increases or decreases significantly in comparison with those in a healthy subject. Therefore, according to the method of the present invention, it can be determined that the subject may be healthy when the expression level of the surface antigen is not less than the reference value or not more than the reference value and that the subject may be suffering from FMS when the expression level of the surface antigen is less than the reference value or more than the reference value.

Furthermore, regarding $CD4^-CD8^-$ MAITs, the expression level of one or more surface antigens selected from the group consisting of CCR4, CXCR1 and CD107a in a FMS patient decreases significantly in comparison with that in a healthy subject. Therefore, according to the method of the present invention, it can be determined that the subject may be healthy when the expression level of the surface antigen is not less than the reference value and that the subject may be suffering from FMS when the expression level of the surface antigen is less than the reference value.

For the reference value, a cutoff value appropriately established for enabling differentiation of a FMS patient from a healthy subject can be used.

In another specific embodiment, the method of the present invention is a method for differentiating a FMS patient from a RA patient. In this case, it is possible to differentiate a FMS patient from a RA patient by measuring the expression level of CD44 or CXCR1, or both CD44 and CXCR1 (Table 6 and FIGS. 3E and F).

For example, regarding the total MAITs ($CD4^+$, $CD8^+$, and DN cells), the expression level of CD44 in a FMS patient decreases significantly in comparison with that in a RA patient. Therefore, according to the method of the present invention, it can be determined that the subject may be suffering not from FMS but from RA when the expression level of CD44 is not less than the reference value and that the subject may be suffering not from RA but from FMS when the expression level of CD44 is less than the reference value.

Furthermore, regarding DN ($CD4^-CD8^-$) MAITs, the expression level of CXCR1 in a FMS patient decreases significantly in comparison with that in a RA patient. Therefore, according to the method of the present invention, it can be determined that the subject may be suffering not from FMS but from RA when the expression level of the CXCR1 is not less than the reference value and that the subject may be suffering not from RA but from FMS when the expression level of the CXCR1 is less than the reference value.

For the reference value, a cutoff value appropriately established for enabling differentiation of a FMS patient from a RA patient can be used.

In still another specific embodiment, the method of the present invention is a method for differentiating a FMS patient from a SpA patient. In this case, it is possible to differentiate a FMS patient from a SpA patient by measuring the expression level of CXCR4 (Table 6 and FIG. 3G).

For example, regarding the total MAITs and DN MAITs ($CD4^-CD8^-$), the expression level of CXCR4 in a FMS patient decreases significantly in comparison with that in a SpA patient. Therefore, according to the method of the present invention, it can be determined that the subject may be suffering not from FMS but from SpA when the expression level of CXCR4 is not less than the reference value and that the subject may be suffering not from SpA but from FMS when the expression level of CXCR4 is less than the reference value. For the reference value, a cutoff value appropriately established for enabling differentiation of a FMS patient from a SpA patient can be used.

In still another embodiment, the method of the present invention is a method for differentiating a SpA patient from a healthy subject. In this case, it is possible to differentiate a SpA patient from a healthy subject by measuring the expression level of CD94 in MAITs collected from a human (Table 6A, FIG. 3C).

Figure 4A:
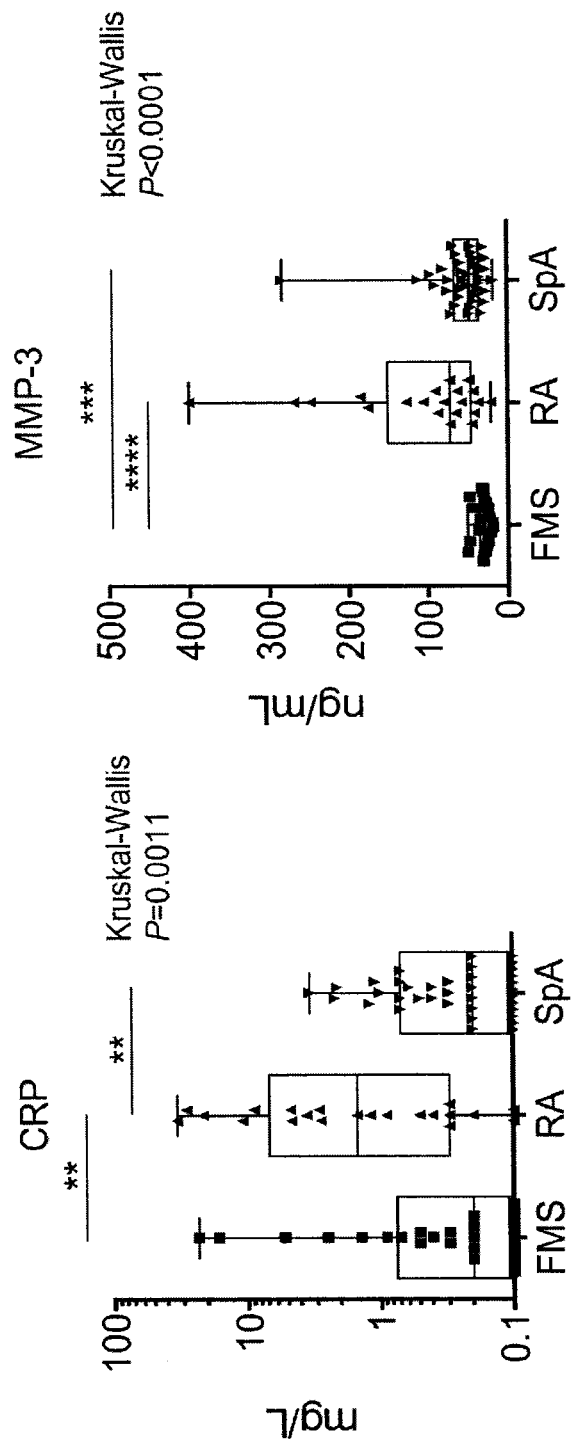
FIG. 4A shows serum C-reactive protein (CRP) concentrations in FMS, RA, and SpA (left panel), and serum matrix metalloproteinase-3 (MMP-3) concentrations in FMS, RA, and SpA (right panel). Horizontal line: Median; boxes: 25th percentile and 75th percentile; whiskers: Minimum and Maximum (the same applies to FIG. 4B). Asterisk shows the group-pairs exhibiting significance (the same applies to FIG. 4B). *: P<0.05, : P<0.01, *: P<0.001 (P value adjusted after the Kruskal-Wallis test with the Dunn's multicomponent test) (the same applies to FIG. 4B).

The present invention also provides a method for diagnosing FMS, the method comprising measurement of the amount of CRP or MMP-3, or both CRP and MMP-3 in the aforementioned biological sample (e.g., a blood sample). The present method may be applied in combination with the aforementioned method. The measurement of the amount can be carried out similarly to the aforementioned measurement of the expression level of protein. According to the present method, FMS can be differentiated from RA and/or SpA (FIG. 4A, and Tables 7 and 8). The expression level of CRP and MMP-3 in a FMS patient is significantly low in comparison with that in RA and/or SpA patients. Therefore, according to the method of the present invention, it can be determined that the subject may be suffering not from FMS but from RA and/or SpA when the amounts of CRP and MMP-3 are not less than the reference values and that the subject may be suffering not from RA and/or SpA but from FMS when the amounts of CRP and MMP-3 are less than the reference values. For the reference values, cutoff values appropriately established for enabling to differentiate a FMS patient from a RA patient and/or a SpA patient can be used. Further, according to the present invention, it is also possible to differentiate RA from FMS and/or SpA, and to differentiate SpA from FMS and/or RA, for example, by measuring the amount of CRP or MMP-3 or both CRP and MMP-3.

The present invention can also be used for determining the therapeutic effect of a drug. For example, it is possible to determine the pain level of a FMS patient by measuring the relative frequency of MAITs to the total T cells, and thus, it is possible to determine the pain relief effect of the drug by using such a frequency as an index. Further, the level of the surface antigens vary in a FMS patient with respect to a healthy subject. Therefore, the therapeutic effect of a drug can be determined by monitoring the change in expression level of the surface antigen before, after or during a treatment with the drug, for example, by assessing whether the expression level of the surface antigen specific to a FMS patient can be restored to that in a healthy subject.

The present invention also comprises a diagnosis kit for FMS, the kit comprising a means for measuring (1) the relative frequency of MAITs to the total T cells in a sample; or (2) the expression level of one or more surface antigens selected from the group consisting of CD4, CD8, CCR4, CCR7, CXCR1, NKp80, CD150, CD107a, CD8β, CD44 and CXCR4, for MAITs in a sample, wherein the sample is collected from a human.

In one embodiment, the diagnostic kit of the present invention comprises a means for measuring the relative frequency of MAITs to the total T cells, in a biological sample collected from a human. An example of the means for measuring the relative frequency of the MAITs to the total T cells is a combination of a means for measuring T cell marker (e.g., CD3) and a means for measuring MAIT cell markers (e.g., Vα7.2-Jα33, CD161). An example of the means for measuring a marker is a means for measuring a gene expression level or a protein amount (e.g., two or more primers, a probe, an antibody or an aptamer). Preferably, the measuring means is an antibody, but not limited thereto. Further, an example of a means for measuring MAIT cell markers is a MR-1 tetramer molecule loaded with vitamin $B_2$ derivatives or with antagonists, which are antigens recognized by Vα7.2. Any means capable of recognizing the MAITs can be used as a means for measuring the relative frequency of MAITs.

For example, the diagnosis kit of the present invention is a kit for determining the pain level of a FMS patient, and the kit comprises a means for measuring an relative frequency of the MAITs to the total T cells. In this case, the diagnosis kit of the present invention comprises a means for measuring a T cell marker (e.g., CD3) and a means for measuring MAIT cell markers (e.g., Vα7.2-Jα33, CD161), both of which are used for measuring the relative frequency of MAITs to the total T cells.

Further, the diagnosis kit of the present invention is a kit for differentiating a FMS patient from a healthy subject, and it comprises a means for measuring the relative frequency of $CD4^+$ MAITs to the total T cells. In this case, the diagnosis kit of the present invention comprises a means for measuring a T cell marker (e.g., CD3), and a means for measuring MAIT cell marker (e.g., Vα7.2-Jα33, CD161) along with a means for measuring CD4 as a classification marker for MAITs, which are the means for measuring the relative frequency of $CD4^+$ MAITs to the total T cells.

In another embodiment, the diagnosis kit of the present invention comprises a means for measuring one or more surface antigens selected from the group consisting of CD4, CD8, CCR4, CCR7, CXCR1, NKp80, CD150, CD107a, CD8β, CD44 and CXCR4 for MAITs in a biological sample collected from a human. The diagnosis kit of the present invention may comprise a combination of a means for measuring one or more classification markers (e.g., CD4, CD8) of MAITs and a means for measuring one or more surface antigens selected from the group consisting of CCR4, CCR7, CXCR1, NKp80, CD150, CD107a, CD8β, CD44 and CXCR4. An example of the means for measuring the surface antigens is a means for measuring a gene expression level or a protein amount (e.g., two or more primers, a probe, an antibody, or an aptamer). The diagnosis kit may further comprise a means for measuring a T cell marker (e.g., CD3) and/or a means for measuring MAIT cell markers (e.g., Vα7.2-Jα33, CD161) as mentioned above. Preferably, the measuring means is an antibody.

In a specific embodiment, the diagnosis kit of the present invention is a kit for differentiating a FMS patient from a healthy subject. In this case, the diagnosis kit of the present invention comprises a means for measuring one or more surface antigens selected from the group consisting of CD4, CD8, CCR4, CCR7, CXCR1, NKp80, CD150, CD107a and CD8β.

For example, regarding MAITs (CD4$^+$, CD8$^+$ and DN MAITs), the expression level of one or more surface antigens selected from the group consisting of CCR4, CCR7, CXCR1, NKp80, CD150 and CD8β in a FMS patient increases or decreases significantly in comparison with that in a healthy subject. Therefore, the diagnosis kit of the present invention may comprise a means for measuring MAIT cell markers (e.g., Vα7.2-Jα33, CD161) and a means for measuring one or more surface antigens selected from the group consisting of CCR4, CCR7, CXCR1, NKp80, CD150 and CD8β.

Further, regarding CD8$^+$ MAITs, the expression level of one or more surface antigens selected from the group consisting of CCR7, NKp80, CD150 and CD8β in a FMS patient increases or decreases significantly in comparison with that in a healthy subject. Therefore, the diagnosis kit of the present invention may comprise a means for measuring MAIT cell markers (e.g., Vα7.2-Jα33, CD161), a means for measuring CD8, and a means for measuring one or more surface antigens selected from the group consisting of CCR7, NKp80, CD150 and CD8β.

Further, regarding DN (CD4$^-$CD8$^-$) MAITs, the expression level of one or more surface antigens selected from the group consisting of CCR4, CXCR1 and CD107a in a FMS patient decreases significantly in comparison with that in a healthy subject. Therefore, the diagnosis kit of the present invention may comprise a means for measuring MAIT cell markers (e.g., Vα7.2-Jα33, CD161), a means for measuring CD4 and CD8, and a means for measuring one or more surface antigens selected from the group consisting of CCR4, CXCR1 and CD107a.

In another specific embodiment, the diagnosis kit of the present invention is a kit for differentiating a FMS patient from a RA patient. In this case, the diagnosis kit of the present invention comprises a means for measuring CD44 or CXCR1, or both CD44 and CXCR1.

For example, regarding the total MAITs (CD4$^+$, CD8$^+$, and DN MAITs), the expression level of CD44 in a FMS patient decreases significantly in comparison with that in a RA patient. Therefore, the diagnosis kit of the present invention may comprise a means for measuring MAIT cell markers (e.g., Vα7.2-Jα33, and CD161) and a means for measuring CD44.

Furthermore, regarding DN (CD4$^-$CD8$^-$) MAITs, the expression level of CXCR1 in a FMS patient decreases significantly in comparison with that in a RA patient. Therefore, the diagnosis kit of the present invention may comprise a means for measuring MAIT cell markers (e.g., Vα7.2-Jα33, CD161), a means for measuring CD4 and CD8, and a means for measuring CXCR1.

In still another embodiment, the diagnosis kit of the present invention is a kit for differentiating a FMS patient from a SpA patient. In this case, the diagnosis kit of the present invention comprises a means for measuring CXCR4.

For example, regarding the DN MAITs (CD4$^-$CD8$^-$), the expression level of CXCR4 in a FMS patient decreases significantly in comparison with that in a SpA patient. Therefore, the diagnosis kit of the present invention may comprise a means for measuring MAIT cell markers (e.g., Vα7.2-Jα33, CD161) and a means for measuring CXCR4.

Further, the present invention provides a FMS diagnosis kit comprising a means for measuring CRP or MMP-3, or both CRP and MMP-3 in the aforementioned biological sample (e.g., a blood sample). Components of the diagnosis kit may be comprised as components of the aforementioned diagnosis kit. The diagnosis kit enables to differentiate FMS from RA and/or SpA. Further, the diagnosis kit enables to differentiate RA from FMS and/or SpA, and to differentiate SpA from FMS and/or RA.

The aforementioned measuring means may be linked to a detection substance. The measuring means can be linked directly or indirectly (i.e., by use of a linker) to the detection substance. Examples of the detection substance include an enzyme (e.g., horseradish peroxidase, alkaline phosphatase), an affinity substance (e.g., streptavidin, biotin), a fluorescent substance (e.g., fluorescein, fluorescein isothiocyanate, rhodamine), a luminescent substance (e.g., luciferin, aequorin) and a radioactive substance.

The aforementioned measuring means may be fixed onto a solid phase. Examples of the solid phase include a membrane (e.g., nitrocellulose membrane), particles, a plate (e.g., a multi-well plate), and a device (e.g., MAIT cell separation device). Examples of the material for the solid phase include a polymeric substance, a magnetic substance, glass, and a metal.

The aforementioned diagnosis kit of the present invention is useful for carrying out the method of the present invention, for example.

EXAMPLES

The present invention will be described below with reference to the following Examples, but the present invention is not limited by these Examples.

The following abbreviations are used for the terms frequently used in the following Examples.

FMS: fibromyalgia syndrome
RA: rheumatoid arthritis
SpA: spondyloarthritis
HD: healthy subject
MAITs: mucosal-associated invariant T cells
DN MAITs: CD4 and CD8-double negative MAITs (CD4$^-$CD8$^-$ MAIT cell)

1. Method 1-1) Patients

The subjects consisted of 26 FMS, 21 RA, and 37 SpA patients, and 16 HD. Characteristics of the patients are summarized in Table 1. All FMS patients met the ACR criteria [Hauser W et al. (2012) Reumatismo 64: 194-205; and Scott D L et al. (2010) Lancet 376: 1094-1108]. Patients having comorbidity, such as HIV, diabetes, peripheral neuropathy, demyelinating disorders (e.g., multiple sclerosis) and inflammatory rheumatic diseases (e.g., RA, SpA, and polymyalgia rheumatica) were excluded from the FMS group. RA was diagnosed according to the 1987 ACR criteria [Scott D L et al. (2010) Lancet 376: 1094-1108]. All SpA patients satisfied the standard set by the European Spondylarthropathy Study Group and/or those modified by the New York criteria [Dougados M et al., (2011) Lancet 377: 2127-2137]. All FMS patients developed primary FMS, and All RA, SpA, and FMS patients received no biological treatments (e.g., anti-TNF-α or anti-IL-6 monoclonal antibodies). No SpA patient carried HLA-B 27.

TABLE 1

Characteristics of the patients

|  | FMS | RA | SpA | HD |
|---|---|---|---|---|
| Number of the patients | 26 | 21 | 37 | 16 |
| SpA subgroups, N |  |  |  |  |
| AS[1] | N/A[8] | N/A | 17 | N/A |
| uSpA[2] | N/A | N/A | 17 | N/A |
| PAO[3] | N/A | N/A | 1 | N/A |
| Re-Arth[4] | N/A | N/A | 2 | N/A |
| Age at sampling, mean ± SD (years) | 46.4 ± 14.0 | 59.8 ± 12.8 | 52.5 ± 11.3 | 45.0 ± 12.4 |
| Sex, N male/female | 1/25 | 2/19 | 6/31 | 2/14 |
| FIQ[5] score, median (25th-75th percentile) | 30.6 ± 28.2 | N/A | N/A | N/A |
| BASDAI[6], median (25th-75th percentile) | N/A | N/A | 5.2 ± 2.0 | N/A |
| BASFI[7], median (25th-75th percentile) | N/A | N/A | 4.1 ± 2.4 | N/A |
| Drug treatments, |  |  |  |  |
| (% of the patients) | 0.0 | 71.4 | 16.2 | N/A |
| methotrexate | 0.0 | 9.5 | 51.4 | N/A |
| sulfasalazine | 11.5 | 57.1 | 48.6 | N/A |
| cortico steroid | 61.5 | 0.0 | 24.3 | N/A |
| anti-convulsant | 42.3 | 4.8 | 5.4 | N/A |
| anti-depressant | 38.5 | 0.0 | 29.7 | N/A |
| opiate | 61.5 | 19.0 | 10.8 | N/A |
| neurotropin | 0.0 | 23.8 | 0.0 | N/A |
| others | 3.8 | 0.0 | 0.0 | N/A |
| no treatment |  |  |  |  |

SpA was subtyped as indicated. Disease indexes, such as FIQ, BASDAI, and BASFI, are shown where applicable.
HD: healthy subjects,
FMS: fibromyalgia syndrome,
RA: rheumatoid arthritis,
SpA: spondyloarthritis.
Data are shown with median (25th-75th percentile), except the age data with mean (± standard deviation (SD)). Almost all FMS patients were subjected to drug treatment.
[1]AS, ankylosing arthritis
[2]uSpA, undifferentiated spondyloarthritis
[3]PAO, pustulotic arthro-osteitis
[4]Re-Arth, reactive arthritis
[5]FIQ, fibromyalgia Impact Questionnaire
[6]BASDAI, bath ankylosing spondylitis disease activity index
[7]BASFI, bath ankylosing spondylitis functional index
[8]N/A, not applicable 1-2) Ethics Approval Institutional review board or ethics committee approval (Graduate School of Medicine, Hokkaido University and Tokeidai Memorial Clinic) and patient written informed consent were obtained before study participation according to the Declaration of Helsinki.

1-3) Samples

Peripheral blood mononuclear cells (PBMCs) from FMS, RA, SpA, and HD were prepared using a Ficoll gradient and subjected to 8-color fluorescence-activated cell sorting (FACS) analysis, as described previously except that the MACSQuant (Miltenyi, Germany) equipped with a 605 nm filter was used [Wakao H et al. (2013) Cell Stem Cell 12: 546-558]. Cell surface antigen expression was analyzed with the indicated phycoerythrin (PE)-labeled anti-human antibody within Brilliant Violet 421-labeled CD3$^+$, Allophycocyanin (APC)-labeled CD161$^+$, and PE/Cy7- or fluorescein isothiocyanate-labeled (FITC) anti-Vα7.2 (3C10)$^+$-subset. The reaction mixture also contained Brilliant Violet 605-labeled CD4, APC/Cy7-labeled CD8, and FITC- or PE/Cy7-labeled CD45RO. A complete list of PE-labeled cell surface antigens used is provided in Tables 2A and B. Drug administration (treatment) was interrupted for 48 h prior to the sample preparation for 9 FMS patients.

TABLE 2A

List of the cell surface antigens (PE-labeled) used in the study (1)

| chemokine receptors | | | costimulators | | |
|---|---|---|---|---|---|
|  | clone | provider |  | clone | provider |
| CCR2 | 48607 | R & D | GITR | 621 | Biolegend |
| CCR3 | 5E8 | Biolegend | CTLA4 | L3D10 | Biolegend |
| CCR4* | 205410 | R & D | CD27* | O323 | Biolegend |
| CCR5* | HEK/1/85A | Biolegend | CD28* | CD28-2 | Biolegend |
| CCR6* | TG7/CCR6 | Biolegend | CD40L | 24-31 | Biolegend |
| CCR7* | 150503 | R & D | ICOS* | C398.4A | Biolegend |
| CCR8 | 191704 | R & D | CD273 | MIH18 | Biolegend |
| CCR9 | 112509 | R & D | cytokine receptors | | |
| CXCR1* | 8F1/CXCR1 | Biolegend |  | clone | provider |
| CXCR3* | 49801 | R & D | CD25 (IL-2Rα) | BC96 | Biolegend |
| CXCR4* | 12G5 | Biolegend | CD122 (IL-2Rβ) | TU27 | Biolegend |
| CXCR5 | 51505.111 | R & D | CD127 (IL-7Rα)* | A019D5 | Biolegend |
| CXCR6 | 56811 | R & D | IL-12Rβ2 | 305719 | R & D |
| CXCR7 | 8F11-M16 | Biolegend | IL-18Rα* | H44 | Biolegend |
| CX3CR1 | 2A9-1 | MBL | IL-23R | 218213 | R & D |

TABLE 2A-continued

List of the cell surface antigens (PE-labeled) used in the study (1)

| NK receptors | | | CD215 (IL-15Rα) | JM7A4 | Biolegend |
|---|---|---|---|---|---|
| CD56 | clone 39D5 | provider Biolegend | ST2 (IL-33R) | HB12 | MBL |
| | | | SLAM family | | |
| CD94* | DX22 | Biolegend | | clone | provider |
| NKp30 | p30-15 | Biolegend | CD150* | A12(7D4) | Biolegend |
| NKp44 | p44-8 | Biolegend | CD244* | C1.7 | Biolegend |
| NKp46 | 9E2 | Biolegend | | activation marker | |
| NKp80* | 5D12 | Biolegend | | clone | provider |
| NKG2D* | 1D11 | Biolegend | CD69* | FN50 | Biolegend |
| | memory marker | | | Fas-Fas ligand | |
| | Clone | provider | | clone | provider |
| CD62L | DREG-56 | Biolegend | CD95* | DX2 | Biolegend |
| CD44* | BJ18 | Biolegend | CD178 | NOK-1 | Biolegend |
| | integrin family | | | relevant to MAITs | |
| | clone | provider | | clone | provider |
| CD18* | Bu15 | Biolegend | CD26* | BA5b | Biolegend |
| CD49d* | 9F10 | Biolegend | CD243 | UIC2 | Biolegend |
| CD103 | Ber-ACT8 | Biolegend | CD8β* | IVT171 | Biolegend |

Asterisk indicates antigens for which results are shown in FIGS. 2 and 3.

TABLE 2B

List of the cell surface antigens (PE-labeled) used in the study (2)

| cell adhesion | | | TNF-related family | | |
|---|---|---|---|---|---|
| | clone | provider | | clone | provider |
| CD54 | HA58 | Biolegend | CD253 | N2B2 | Biolegend |
| CD57 | HCD57 | Biolegend | CD254 | MIH24 | Biolegend |
| | immuno-regulatory molecules | | CD262 | DJR2-4(7-8) | Biolegend |
| | clone | provider | | Miscellaneous | |
| CD39 | A1 | Biolegend | | clone | provider |
| CD73* | AD2 | Biolegend | CD2* | TS1/8 | Biolegend |
| CD137 | 4B4-1 | Biolegend | CD16 | 3G8 | Biolegend |
| CD137L | 5F4 | Biolegend | CD46 | TRA-2-10 | Biolegend |
| | degranulation | | CD59 | p282(H19) | Biolegend |
| | clone | provider | CD99* | HCD99 | Biolegend |
| CD107a* | H4A3 | Biolegend | | | |

Asterisk indicates antigens for which results are shown in FIGS. 2 and 3.

1-4) Statistics

Statistical analyses of FACS data were performed with GraphPad Prism (ver. 6), and the significance of differences in expression level on the cell surface antigen was evaluated with the nonparametric Mann-Whitney U test, the Kruskal-Wallis test, and the Wilcoxon matched-pairs signed rank test. P values were adjusted with the Dunn's multicomponent test where required. P values<0.05 were considered to indicate statistical significance.

2. Results and Discussion

Figure 1D:
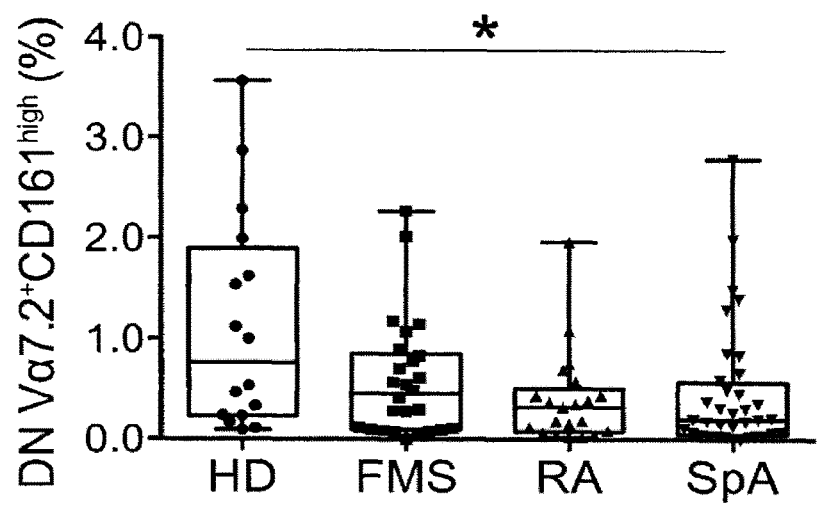
FIG. 1D shows the frequency of DN MAITs in HD, FMS, RA, and SpA. The percentage of DN MAITs (Vα7.2$^+$CD161$^{high}$DN) within the total T cells (CD3$^+$) is shown.
Figure 1E:
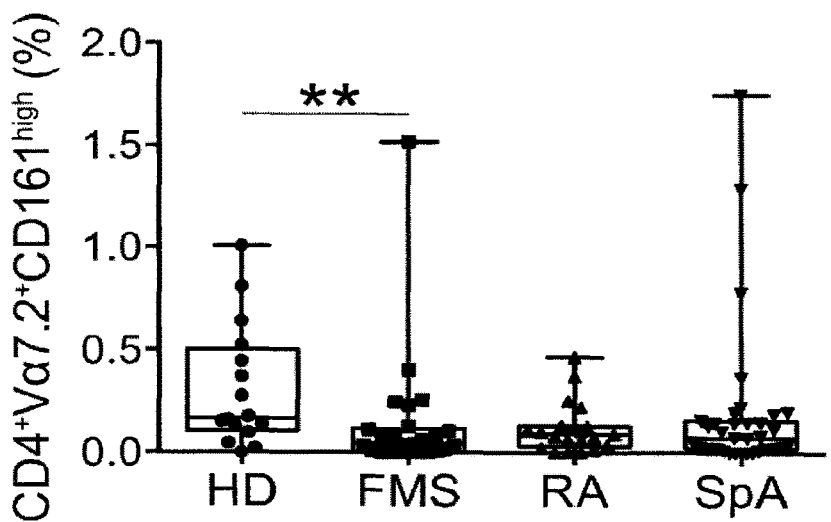
FIG. 1E shows the frequency of CD4$^+$ MAITs in HD, FMS, RA, and SpA. The percentage of CD4$^+$ MAITs (Vα7.2$^+$CD161$^{high}$CD4$^+$) within the total T cells (CD3$^+$) is shown.
Figure 1F:
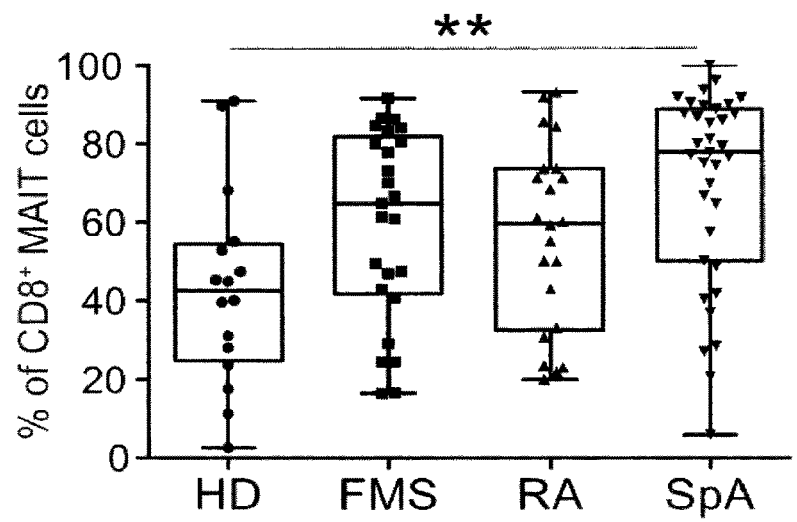
FIG. 1F shows the percentage of CD8$^+$ MAITs (CD8$^+$ Vα7.2$^+$CD161$^{high}$) among total MAITs (Vα7.2$^+$CD161$^{high}$) in HD, FMS, RA, and SpA.
Figure 1G:
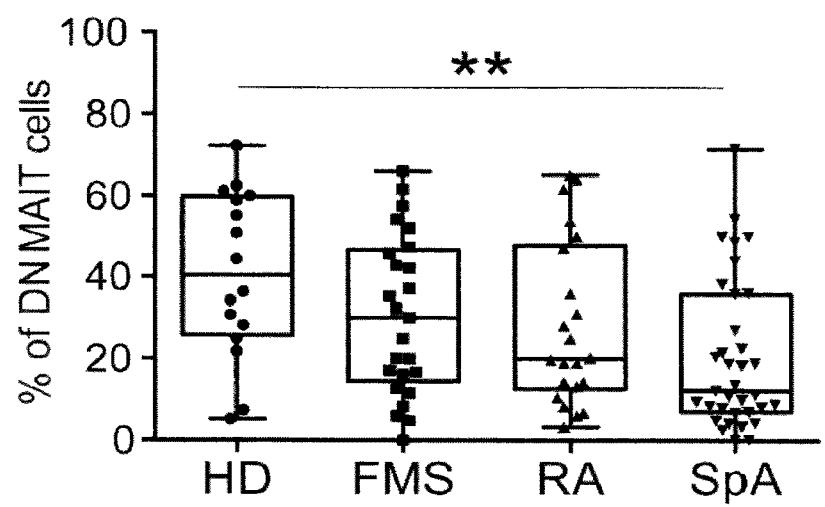
FIG. 1G shows the percentage of DN MAITs (CD8$^-$CD4$^-$ Vα7.2$^+$CD161$^{high}$) among total MAITs (Vα7.2$^+$CD161$^{high}$) in HD, FMS, RA, and SpA.
Figure 1H:
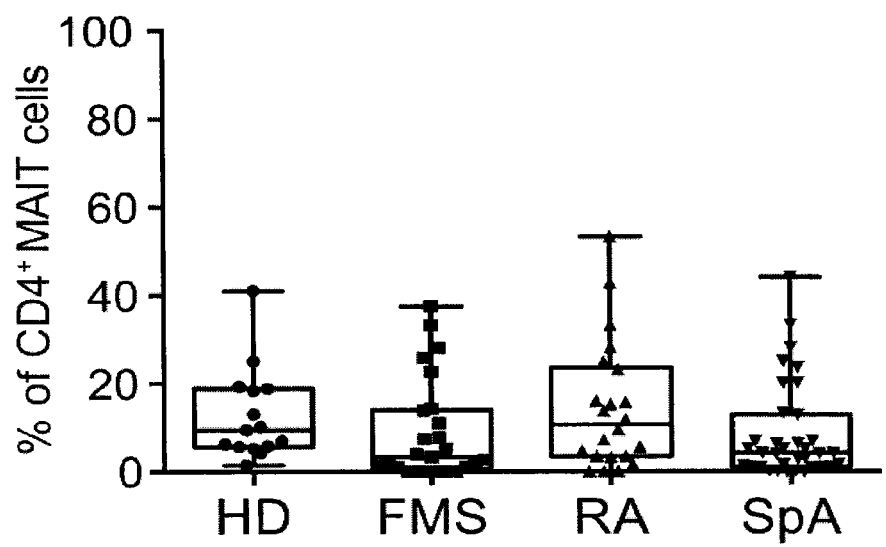
FIG. 1H shows the percentage of CD4$^+$ MAITs (CD4$^+$ Vα7.2$^+$CD161$^{high}$) among total MAITs (Vα7.2$^+$CD161$^{high}$) in HD, FMS, RA, and SpA.
Figure 2A:
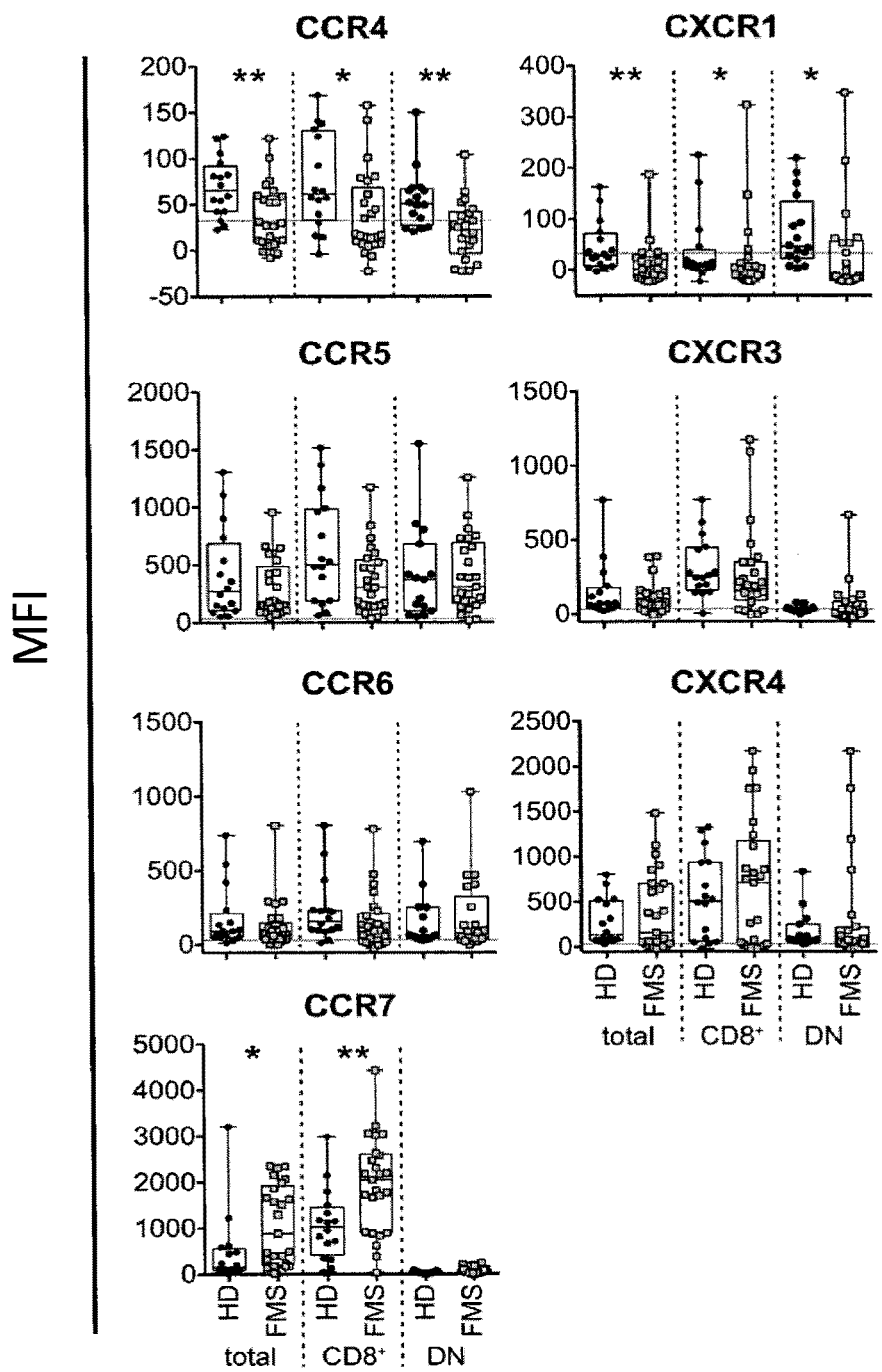
FIG. 2A shows chemokine receptor expression in total, CD8$^+$, and DN MAITs. Mean fluorescent intensity (MFI) is shown with median (the same applies to FIG. 2B-H). The dotted line indicates MFI for the isotype control (the same applies to FIG. 2B-H). Horizontal line: Median; boxes: 25th percentile and 75th percentile; whiskers: Minimum and Maximum (the same applies to FIG. 2B-H). Asterisk shows the group-pair exhibiting significance (the same applies to FIG. 2B-H). *: P<0.05, : P<0.01, *: P<0.001 (the nonparametric Mann-Whitney U test) (the same applies to FIG. 2B-H)
Figure 2B:
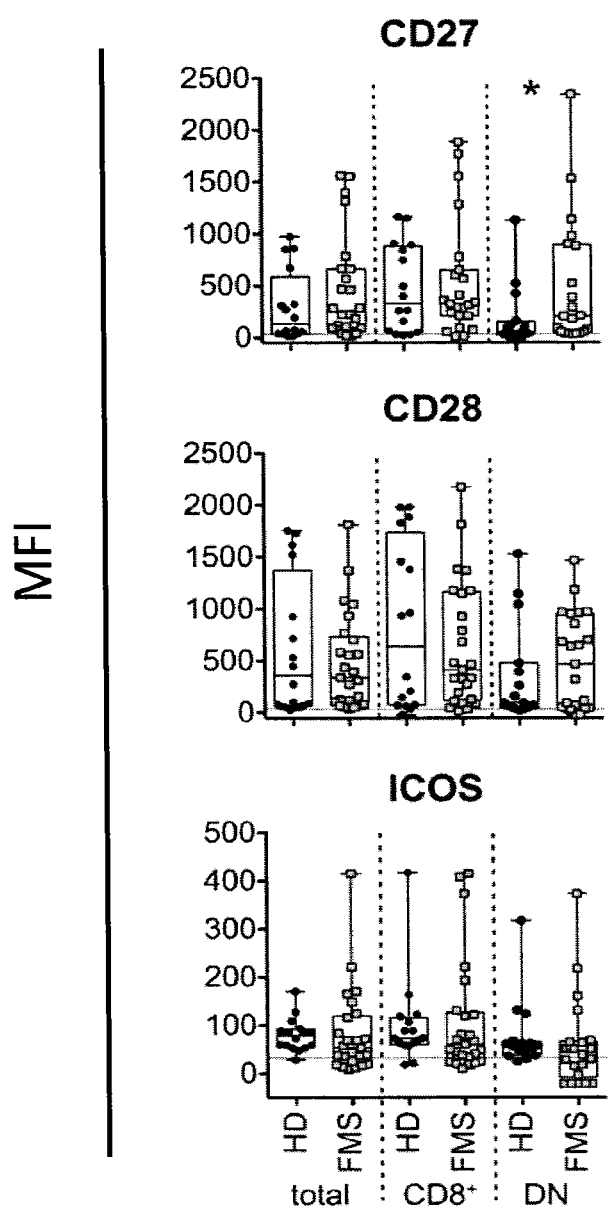
FIG. 2B shows co-stimulatory molecule expression in total, CD8$^+$, and DN MAITs.
Figure 2C:
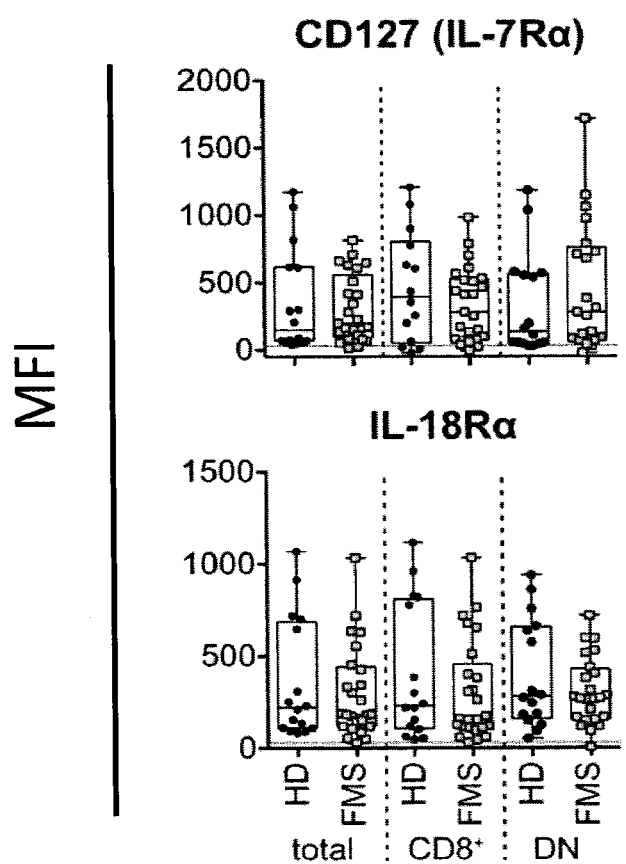
FIG. 2C shows cytokine receptor expression in total, CD8$^+$, and DN MAITs.
Figure 2D:
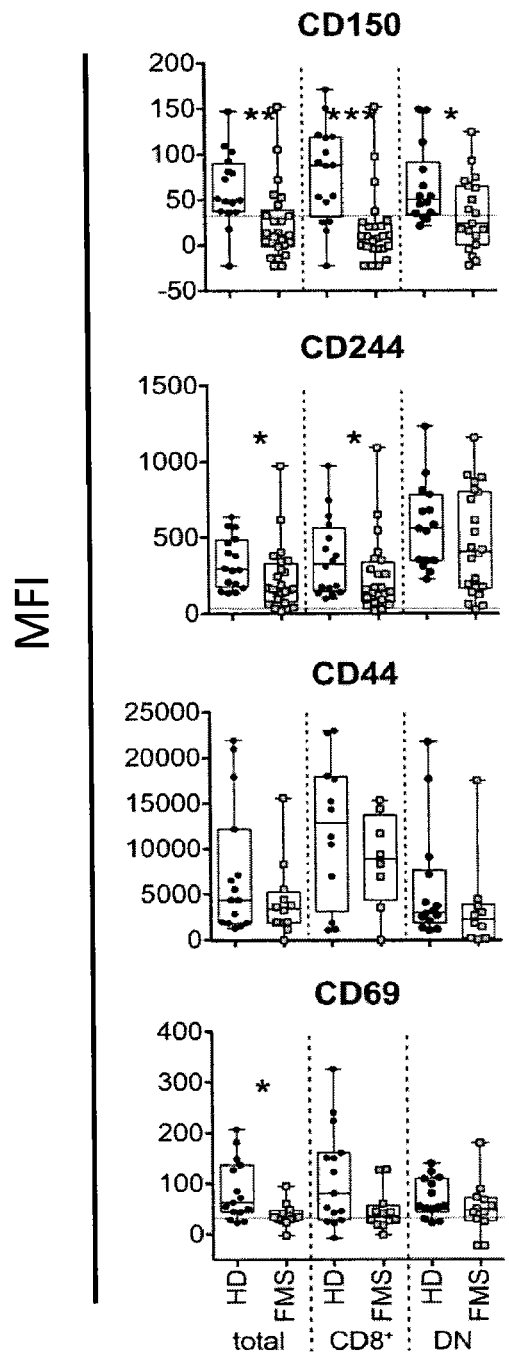
FIG. 2D shows SLAM family, memory, and activation marker expression in total, CD8$^+$, and DN MAITs.
Figure 2E:
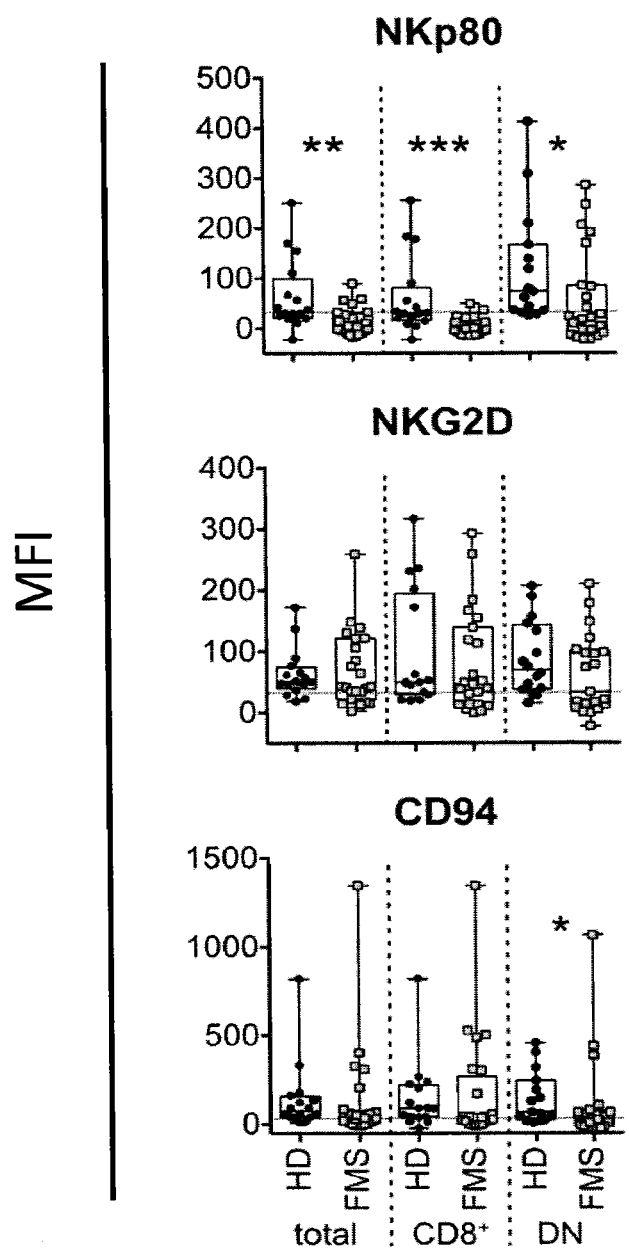
FIG. 2E shows NK receptor expression in total, CD8$^+$, and DN MAITs.
Figure 2F:
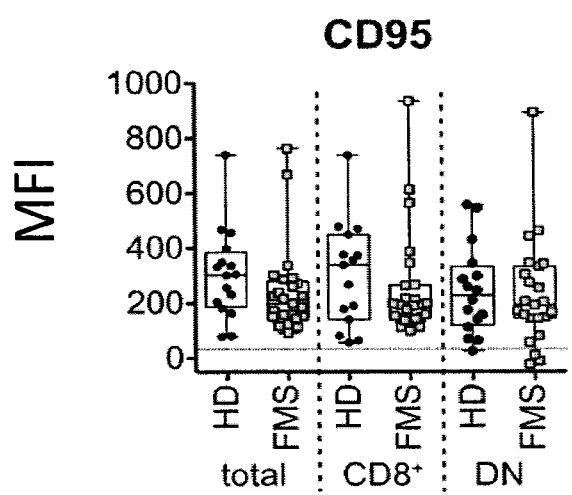
FIG. 2F shows CD95 (Fas) expression in total, CD8$^+$, and DN MAITs.
Figure 2G:
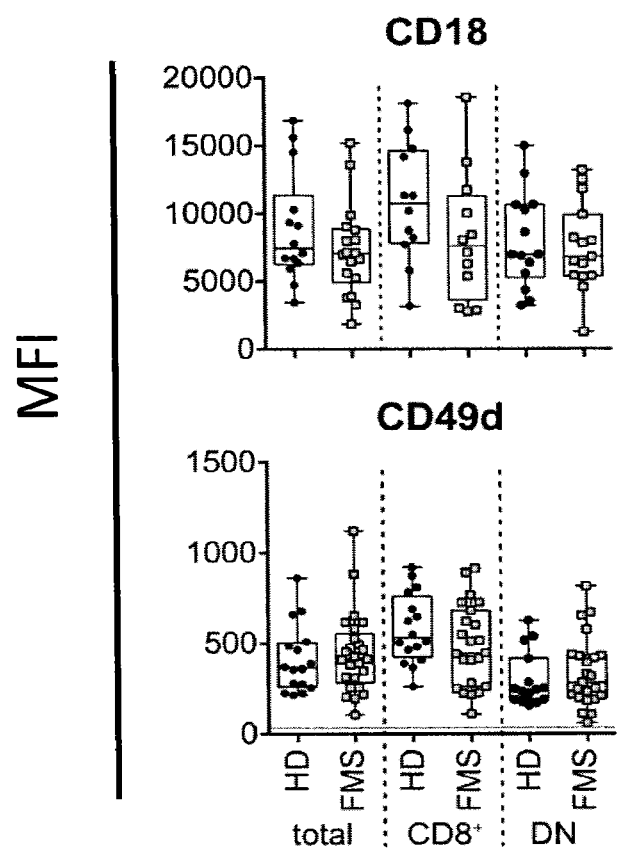
FIG. 2G shows integrin family expression in total, CD8$^+$, and DN MAITs.
Figure 2H:
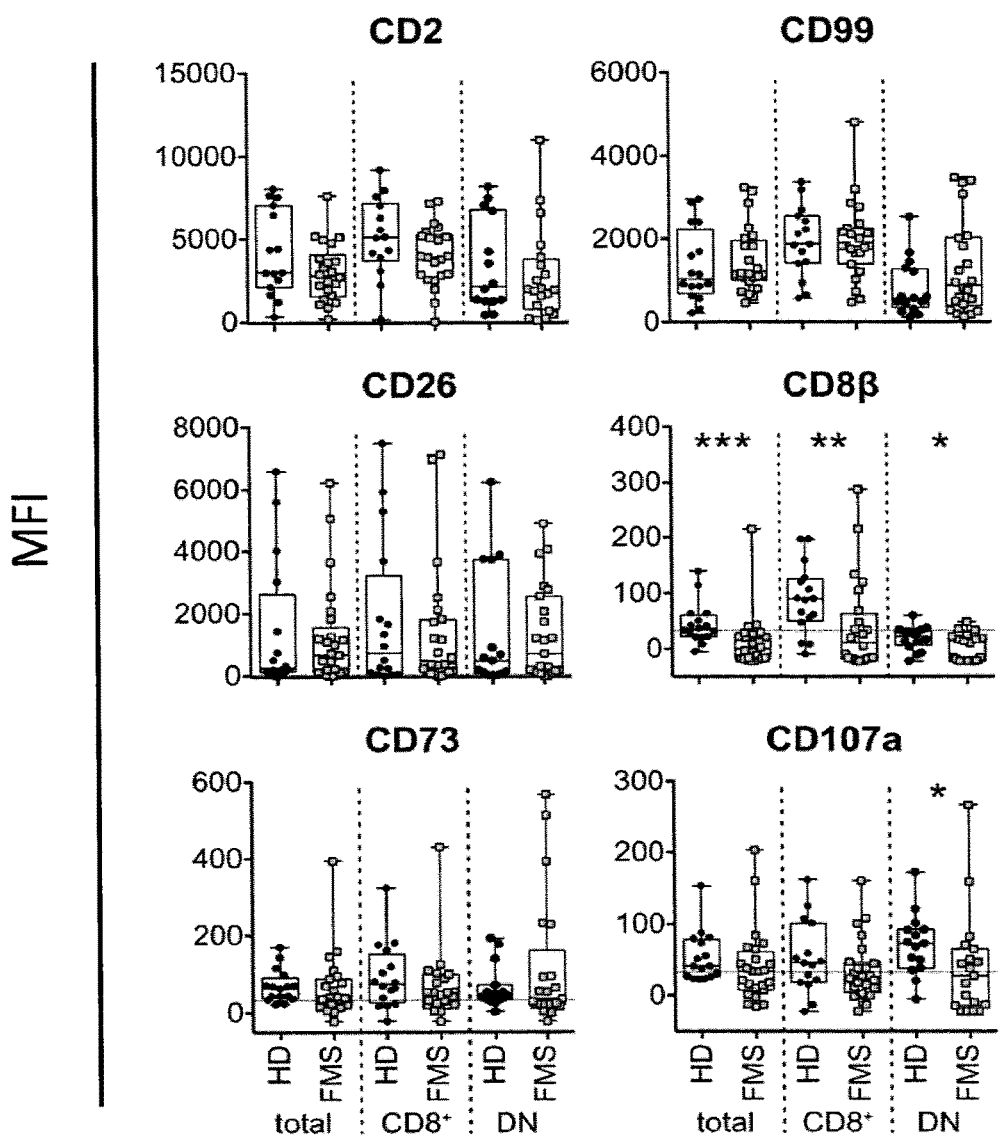
FIG. 2H shows miscellaneous molecule expression in total, CD8$^+$, and DN MAITs.
Figure 3A:
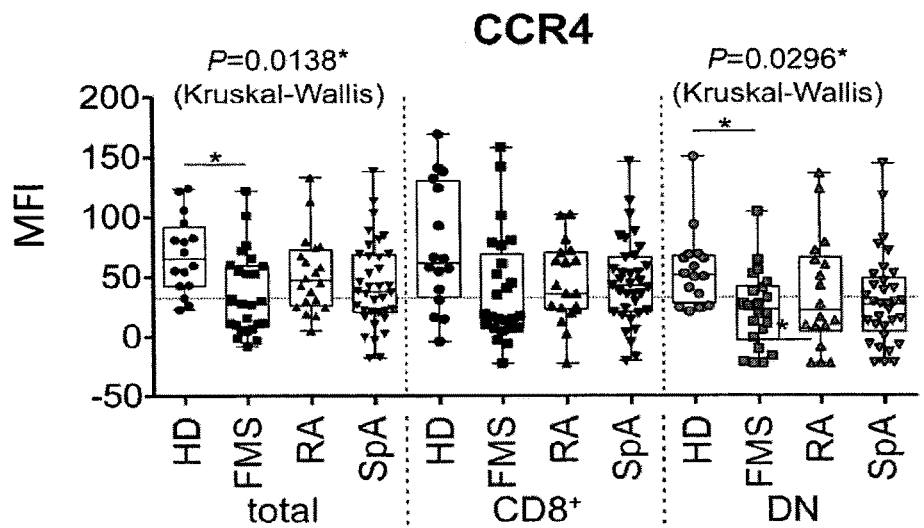
FIG. 3A shows potential biomarkers (CCR4) distinguishing HD, FMS, RA and SpA. MFI is shown with median for the indicated cell surface antigen (the same applies to FIG. 3B-J). The dotted line indicates MFI for the isotype control (the same applies to FIG. 3B-J). Horizontal line: Median; boxes: 25th percentile and 75th percentile; whiskers: Minimum and Maximum (the same applies to FIG. 3B-J). The number in figure shows a P value after the Kruskal-Wallis test (the same applies to FIG. 3B-J). Asterisk shows the group-pairs exhibiting significance (the same applies to FIG. 3B-J). *: P<0.05, : P<0.01, *: P<0.001 (P value adjusted with the Dunn's multicomponent test) (the same applies to FIG. 3B-J). total: total MAITs; CD8+; CD8+ MAITs; DN: DN MAITs (the same applies to FIG. 3B-J).
Figure 3B:
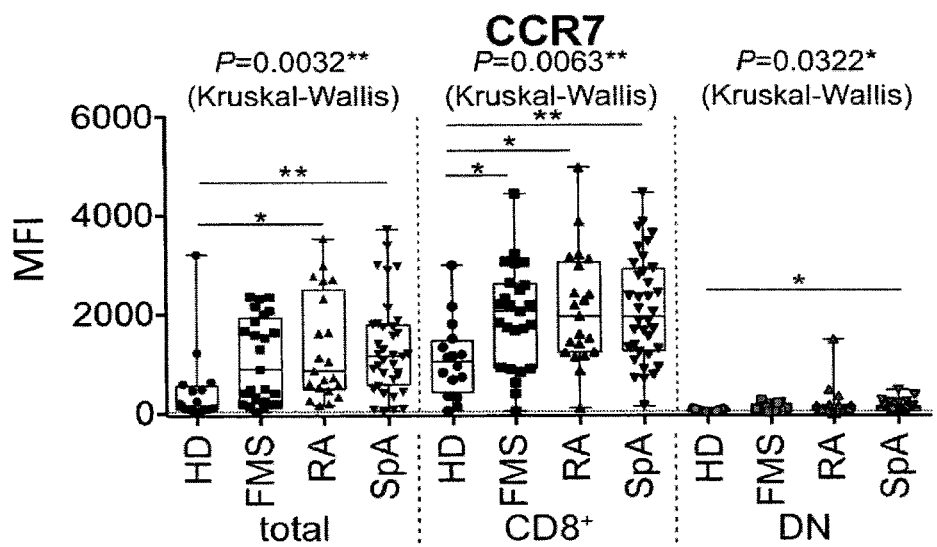
FIG. 3B shows potential biomarkers (CCR7) distinguishing HD, FMS, RA and SpA.
Figure 3C:
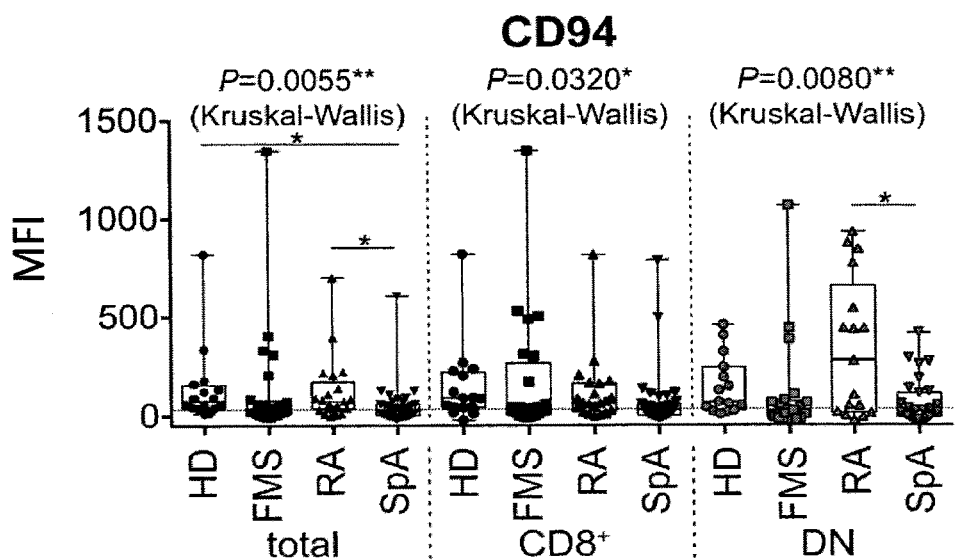
FIG. 3C shows potential biomarkers (CD94) distinguishing HD, FMS, RA and SpA.
Figure 3D:
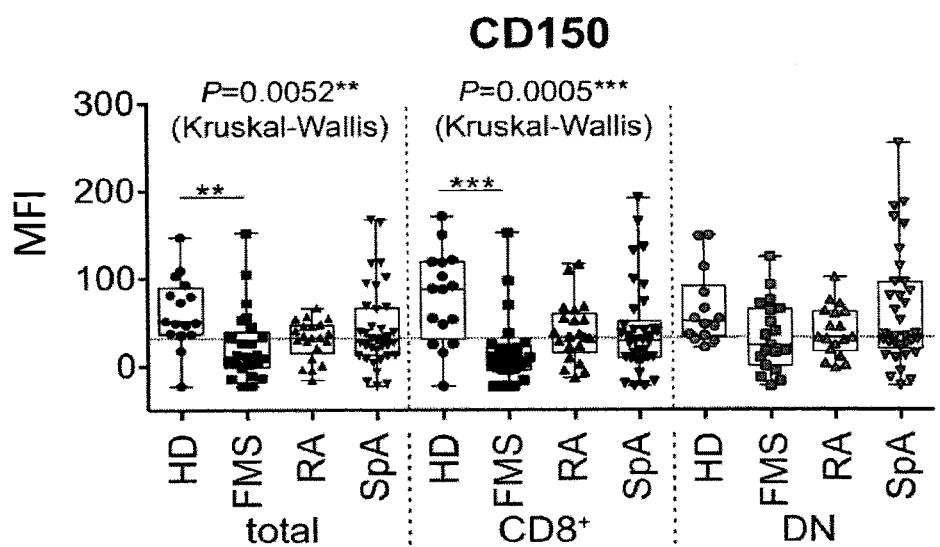
FIG. 3D shows potential biomarkers (CD150) distinguishing HD, FMS, RA and SpA.
Figure 3E:
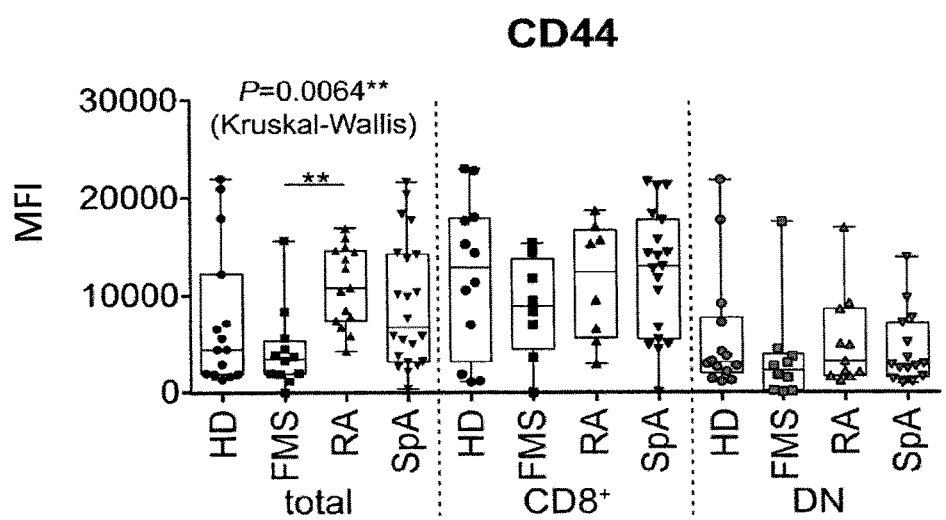
FIG. 3E shows potential biomarkers (CD44) distinguishing HD, FMS, RA and SpA.
Figure 3F:
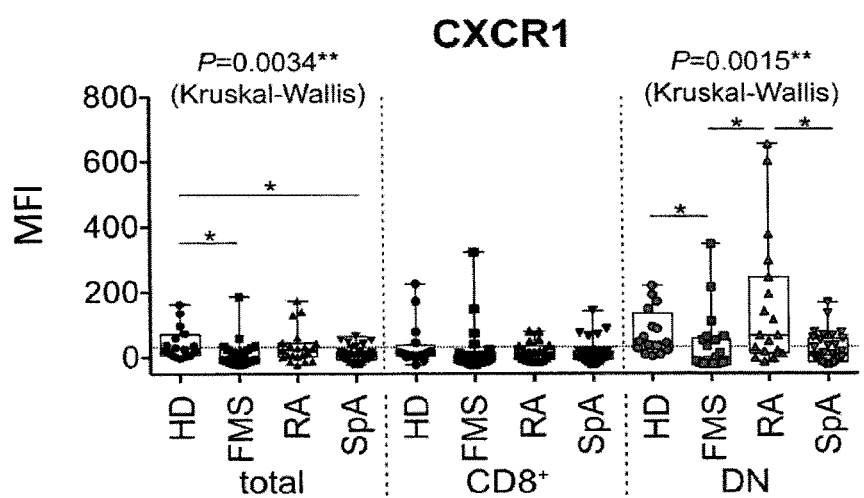
FIG. 3F shows potential biomarkers (CXCR1) distinguishing HD, FMS, RA and SpA.
Figure 3G:
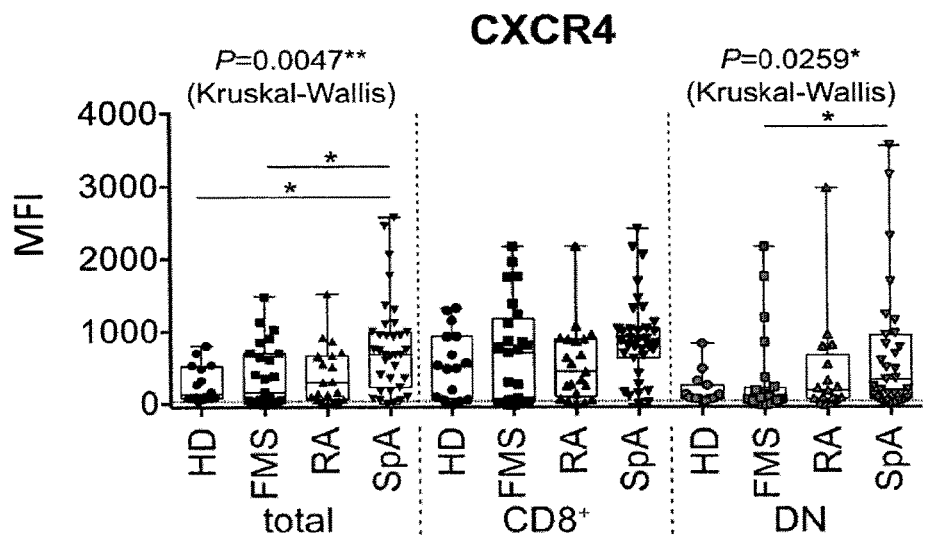
FIG. 3G shows potential biomarkers (CXCR4) distinguishing HD, FMS, RA and SpA.
Figure 3H:
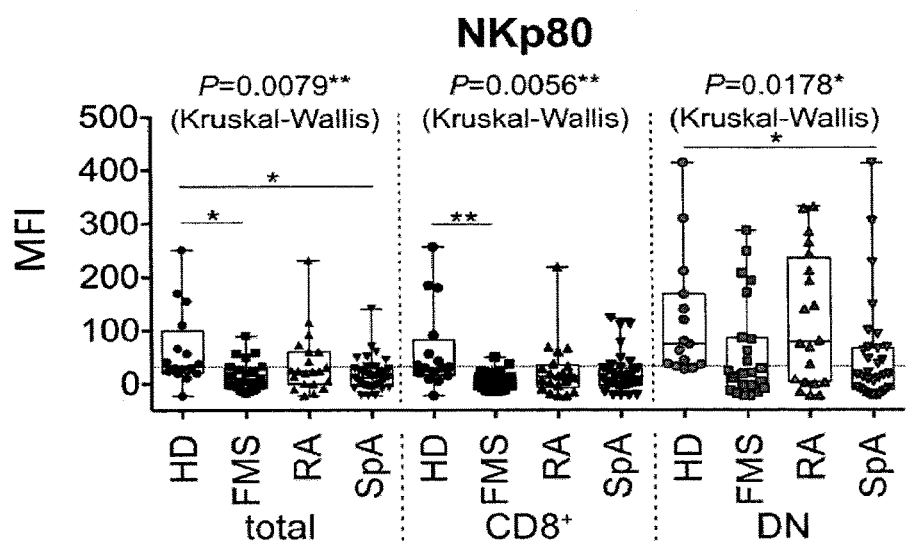
FIG. 3H shows potential biomarkers (NKp80) distinguishing HD, FMS, RA and SpA.
Figure 3I:
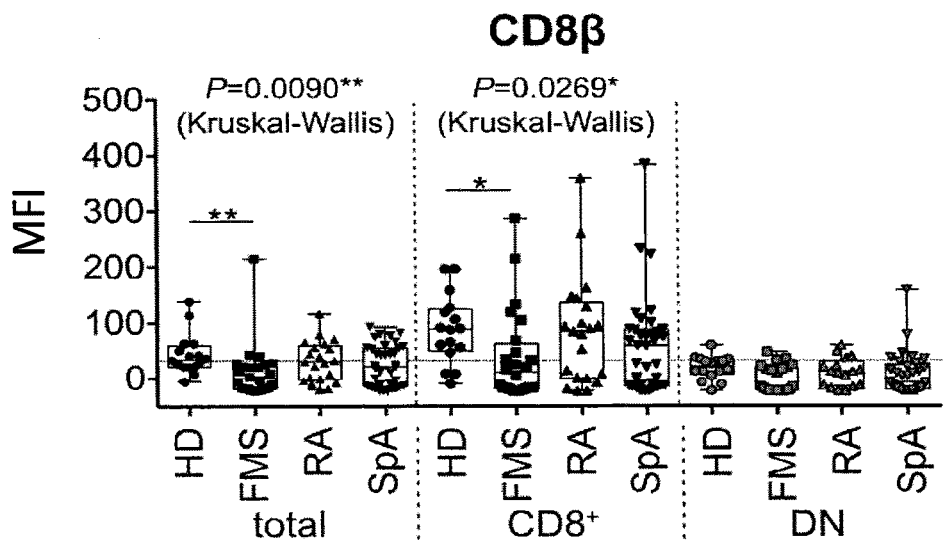
FIG. 3I shows potential biomarkers (CD8β) distinguishing HD, FMS, RA and SpA.
Figure 3J:
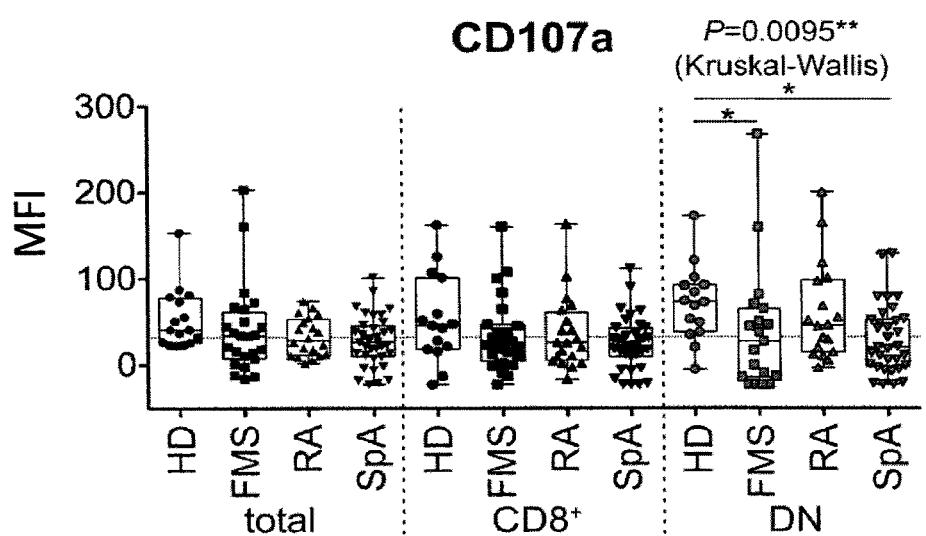
FIG. 3J shows potential biomarkers (CD107a) distinguishing HD, FMS, RA and SpA.

Given that FMS features widespread pain, fatigue, and distressed mood, it has been believed that inflammatory cytokines play a role in triggering neuroendocrine aberrations, eventually leading to these symptoms. Some reports have revealed the aberrant expression of inflammatory cytokines in FMS [Pernambuco A P et al., (2013) Clin Exp Rheumatol 31: S60-S63; Kadetoff D et al. (2012) J Neuroimmunol 242: 33-38; and Sturgill J et al. (2014) J Immunol Res 2014: 938576]. Since the source of cytokines remained unidentified, it is doubtful whether they are potentially useful as a biomarker. Thus, the present inventors analyzed MAITs that produce a plethora of the inflammatory cytokines and chemokines [Wakao H et al. (2013) Cell Stem Cell 12: 546-558]. A representative FACS profile of MAITs and concomitant cell surface antigen expression (NKG2D, a NK receptor) from a FMS patient is shown in FIG. 1A. The present inventors then compared the percentage of total MAITs (defined as $V\alpha7.2^+CD161^{high}$ cells within $CD3^+$ cells) in the diseases, and found that they represented median (25th percentile; 75th percentile): 2.9% (0.9; 4.7), 1.5% (0.8; 2.8), 0.9% (0.4; 2.4), 1.6% (0.6; 2.9) in HD, FMS, RA, and SpA, respectively (FIG. 1B and Table 3). However, there was no statistical significance in difference of the MAIT cell populations among diseases. Because MAITs consist of primarily $CD8^+$ and double negative (DN), and few $CD4^+$ cells [Le Bourhis L at al. (2011) Trends Immunol 32: 212-218], each subset was further analyzed. Difference in MAIT cell frequency was seen in $CD4^+$ and DN MAITs after the Kruskal-Wallis test (Table 4). P value adjustment uncovered that there was a difference in frequency of DN MAITs between HD and SpA and that of $CD4^+$ MAITs between HD and FMS (FIGS. 1D-E and Tables 3 and 4). When the proportion of $CD8^+$, DN, and $CD4^+$ MAITs were analyzed within total MAITs ($V\alpha7.2^+CD161^{high}$ cells), a significant increase in $CD8^+$ MAITs concomitant with a decrease in DN MAITs was observed in SpA as compared with HD (FIG. 1F-G). This suggested that SpA is characterized by the increase in proportion of $CD8^+$ MAITs that is most likely counterbalanced by the decrease of DN MAITs, and such increase can be utilized as a diagnostic marker for distinguishing SpA. In the following experiments, research was performed using total, $CD8^+$, and DN MAITs, as $CD4^+$ MAITs were rare.

TABLE 3

Statistics of the MAIT cell subset frequency (the percentage of total, $CD4^+$, $CD8^+$, and DN MAITs among $CD3^+$ T cells in HD, FMS, RA, and SpA)

| | | Disease | | | |
|---|---|---|---|---|---|
| MAIT cell subsets | statistics subject number | HD 16 | FMS 26 | RA 21 | SpA 36 |
| Total | Minimum | 0.2 | 0.1 | 0.2 | 0.2 |
| ($V\alpha7.2^+CD161^{high}$) | 25% Percentile | 0.9 | 0.8 | 0.4 | 0.6 |
| (%) | Median | 2.9 | 1.5 | 0.9 | 1.6 |
| | 75% Percentile | 4.7 | 2.8 | 2.4 | 2.9 |
| | Maximum | 7.1 | 7.3 | 6.4 | 7.8 |

TABLE 3-continued

Statistics of the MAIT cell subset frequency (the percentage of total, CD4+, CD8+, and DN MAITs among CD3+ T cells in HD, FMS, RA, and SpA)

| MAIT cell subsets | statistics | Disease | | | |
|---|---|---|---|---|---|
| | | HD | FMS | RA | SpA |
| | subject number | 16 | 26 | 21 | 36 |
| CD4+ (%) | Minimum | 0.0 | 0.0 | 0.0 | 0.0 |
| | 25% Percentile | 0.1 | 0.0 | 0.0 | 0.0 |
| | Median | 0.2 | 0.0 | 0.1 | 0.1 |
| | 75% Percentile | 0.5 | 0.1 | 0.1 | 0.2 |
| | Maximum | 1.0 | 1.5 | 0.5 | 1.8 |
| CD8+ (%) | Minimum | 0.1 | 0.0 | 0.1 | 0.1 |
| | 25% Percentile | 0.3 | 0.3 | 0.2 | 0.4 |
| | Median | 0.5 | 0.8 | 0.5 | 1.0 |
| | 75% Percentile | 2.2 | 1.4 | 1.2 | 1.8 |
| | Maximum | 3.2 | 4.1 | 5.9 | 6.8 |
| DN (%) | Minimum | 0.1 | 0.0 | 0.0 | 0.0 |
| | 25% Percentile | 0.2 | 0.1 | 0.1 | 0.0 |
| | Median | 0.8 | 0.5 | 0.3 | 0.2 |
| | 75% Percentile | 1.9 | 0.9 | 0.5 | 0.6 |
| | Maximum | 3.6 | 2.3 | 2.0 | 2.8 |

TABLE 4

Statistics of the MAIT cell subset frequency (p values after the Kruskal-Wallis test among the diseases and adjusted P values)

| MAIT cell subsets | Kruskal-Wallis test (HD, FMS, RA, and SpA) | Adjusted | P value |
|---|---|---|---|
| Total | Ns | ns | |
| CD4+ | 0.0138* | HD vs. FMS | 0.0078** |
| CD8+ | Ns | ns | |
| DN | 0.0229* | HD vs. SpA | 0.0227* |

P values for the difference in frequency of CD4+ and DN MAITs among the subjects are indicated after the Kruskal-Wallis test (middle column). The paired-groups exhibiting a difference in frequency of MAIT cell subsets are shown with P values adjusted with the Dunn's multicomponent test (Adjusted P value) (right column).
Asterisk indicates significance.
ns: not significant.

The present inventors sought that the cell surface antigens in MAITs allow the distinction between HD and FMS. In FMS, the present inventors found a significant increase of CCR7, a chemokine receptor required for lymph node homing, in total MAITs and in CD8+ MAITs and of CD27, a costimulatory molecule for T cell activation, in DN MAITs, compared with HD (FIG. 2A-H and Table 5). In contrast, there was a decrease in two chemokine receptors, CCR4, CXCR1, a natural killer (NK) receptor, NKp80, a signaling lymphocyte associated molecule (SLAM) family, CD150, and a coreceptor, CD8β in all subsets of MAITs, while a decrease in CD244, another SLAM family member, in total and CD8+ MAITs, CD69, an activation marker, in total MAITs, and CD107a in DN MAITs, was seen compared with HD (FIG. 2A-H and Table 5).

TABLE 5

Cell surface antigens showing a difference in expression on MAITs between HD and FMS

| | | P value by Mann-Whitney U test | | |
|---|---|---|---|---|
| categories | Antigens | total | CD8+ | DN |
| chemokine receptors | CCR4 | 0.0033** | 0.0282* | 0.0021** |
| | CCR5 | Ns | ns | Ns |
| | CCR6 | Ns | ns | Ns |
| | CCR7 | 0.0103* | 0.0062** | Ns |
| | CXCR1 | 0.0024** | 0.0207* | 0.0148* |
| | CXCR3 | Ns | ns | Ns |
| | CXCR4 | Ns | ns | Ns |
| Costimulators | CD27 | Ns | ns | 0.0412* |
| | CD28 | Ns | ns | Ns |
| | ICOS | Ns | ns | Ns |
| cytokine receptors | CD127 (IL-7Rα) | Ns | ns | Ns |
| | IL-18Rα | Ns | ns | Ns |
| NK receptors | CD94 | Ns | ns | Ns |
| | NKp80 | 0.0034** | 0.0004*** | 0.0153* |
| | NKG2D | Ns | ns | ns |
| SLAM family | CD150 | 0.0014** | 0.0001*** | 0.0459* |
| | CD244 | 0.0250* | 0.0354* | ns |
| activation marker | CD69 | 0.0190* | ns | ns |
| memory marker | CD44 | Ns | ns | ns |
| Fas | CD95 | Ns | ns | ns |
| integrin family | CD18 | Ns | ns | ns |
| | CD49d | Ns | ns | ns |
| MAIT cell function-related molecule | CD26 | Ns | ns | ns |
| | CD8β | 0.0004*** | 0.0062** | 0.0171* |
| immuno-regulatory molecule | CD73 | Ns | ns | ns |
| miscellaneous | CD2 | Ns | ns | ns |
| | CD99 | Ns | ns | ns |
| degranulation marker | CD107a | Ns | ns | 0.0120* |

P values after comparison between FMS and HD (nonparametric Mann-Whitney U-test) are shown. The category of the cell surface antigens is indicated.
ns: not significant.
Total: total MAITs, CD8+: CD8+ MAITs, DN: DN MAITs.

Next the present inventors tried to find out the cell surface antigens in MAITs that can differentiate HD, FMS, RA, and SpA. As a result, Kruskal-Wallis test has revealed that CCR4, CCR7, CXCR1, CXCR4, CD94, NKp80, CD150, CD44, CD8β, and CD107a are possible markers to distinguish the three diseases (Tables 6A and B, Kruskal-Wallis test). Multiple comparisons after P value adjustment (or after Dunn's multicomponent test) have allowed the identification of CCR4, CCR7, CXCR1, NKp80, CD150, CD8β and CD107a to be potential primary markers for FMS to distinguish from HD, RA and SpA (FIGS. 3A-J and Tables 6A and B, Adjusted P values). In addition, CXCR1 in DN MAITs and CD44 in total MAITs may serve as auxiliary markers to differentiate FMS from RA (FIGS. 3A-J and Tables 6A and B). CXCR4 appeared to be a marker to distinguish SpA from HD in total MAITs, and also be useful to discern FMS and SpA in total and DN MAITs (FIGS. 3A-J and Tables 6A and B). Among the cell surface molecules so far studied, CD94 in total and DN MAITs, and CXCR1 in DN MAITs, would allow the distinction between RA and SpA (FIGS. 3A-J and Tables 6A and B).

TABLE 6A

Cell surface antigens distinguishing HD, FMS, RA, and SpA

| categories | antigens | Kruskal-Wallis (HD, FMS, RA, and SpA) MAITs total | CD8+ | DN | Adjusted P value MAITs total | | CD8+ | | DN | |
|---|---|---|---|---|---|---|---|---|---|---|
| chemokine receptors | CCR4 | 0.0138* | ns | 0.0296* | HD vs. FMS | 0.0111* | ns | | HD vs. FMS | 0.0269* |
| | CCR5 | ns | ns | ns | ns | | ns | | ns | |
| | CCR6 | ns | ns | ns | ns | | ns | | ns | |
| | CCR7 | 0.0032** | 0.0063** | 0.0322* | HD vs. FMS | 0.0102* | HD vs. FMS | 0.0347* | HD vs. SpA | 0.0333* |
| | | | | | HD vs. RA | 0.0026** | HD vs. RA | 0.0186* | | |
| | | | | | | | HD vs. SpA | 0.0062** | | |
| | CXCR1 | 0.0034** | ns | 0.0015** | HD vs. FMS | 0.0140* | ns | | HD vs. FMS | 0.0474* |
| | | | | | HD vs. SpA | 0.0143* | | | FMS vs. RA | 0.0169* |
| | | | | | | | | | RA vs. SpA | 0.0237* |
| | CXCR3 | ns | ns | ns | ns | | ns | | ns | |
| | CXCR4 | 0.0047** | ns | 0.0259* | HD vs. SpA | 0.0438* | ns | | FMS vs. SpA | 0.0201* |
| | | | | | FMS vs. SpA | 0.0161* | | | | |
| costimulators | CD27 | ns | ns | ns | ns | | ns | | ns | |
| | CD28 | ns | ns | ns | ns | | ns | | ns | |
| | ICOS | ns | ns | ns | ns | | ns | | ns | |
| cytokine receptors | CD127 (IL-7Rα) | ns | ns | ns | ns | | ns | | ns | |
| | IL-18Rα | ns | ns | ns | ns | | ns | | ns | |
| NK receptors | CD94 | 0.0055** | 0.0320* | 0.0080* | HD vs. SpA | 0.0191* | ns | | RA vs. SpA | 0.0304* |
| | | | | | RA vs. SpA | 0.0365* | | | | |
| | NKp80 | 0.0079** | 0.0056** | 0.0178* | HD vs. FMS | 0.0138* | HD vs. FMS | 0.0025** | HD vs. SpA | 0.0362* |
| | | | | | HD vs. SpA | 0.0189* | | | | |
| | NKG2D | ns | ns | ns | ns | | ns | | ns | |

P values for the indicated antigens as a diagnostic indicator after all possible multiple comparisons between the groups (Kruskal-Wallis test), and after adjustment with the Dunn's multicomponent test (Adjusted P value) are shown. Group pairs showing a significant difference are also depicted (Adjusted P value).
ns: not significant.
total: total MAITs,
CD8+: CD8+ MAITs,
DN: DN MAITs.

TABLE 6B

Cell surface antigens distinguishing HD, FMS, RA, and SpA

| categories | antigens | Kruskal-Wallis (HD, FMS, RA, and SpA) MAITs total | CD8+ | DN | Adjusted P value MAITs total | | CD8+ | | DN |
|---|---|---|---|---|---|---|---|---|---|
| SLAM family | CD150 | 0.0052** | 0.0005*** | ns | HD vs. FMS | 0.0022** | HD vs. FMS | 0.0002*** | ns |
| | CD244 | ns | ns | ns | ns | | ns | | ns |
| activation | CD69 | ns | ns | ns | ns | | ns | | ns |
| memory | CD44 | 0.0064** | ns | ns | FMS vs. RA | 0.0052** | ns | | ns |
| Fas | CD95 | ns | ns | ns | ns | | ns | | ns |
| integrin family | CD18 | ns | ns | ns | ns | | ns | | ns |
| | CD49d | ns | ns | ns | ns | | ns | | ns |
| relevant to MAITs | CD26 | ns | ns | ns | ns | | ns | | ns |
| | CD8β | 0.0090** | 0.0269* | ns | HD vs. FMS | 0.0095** | HD vs. FMS | 0.0336* | ns |
| immuno-regulatory molecule | CD73 | ns | ns | ns | ns | | ns | | ns |
| miscellaneous | CD2 | ns | ns | ns | ns | | ns | | ns |
| | CD99 | ns | ns | ns | ns | | ns | | ns |

TABLE 6B-continued

Cell surface antigens distinguishing HD, FMS, RA, and SpA

| categories | antigens | Kruskal-Wallis (HD, FMS, RA, and SpA) MAITs total | CD8+ | DN | Adjusted P value MAITs total | CD8+ | DN | |
|---|---|---|---|---|---|---|---|---|
| degranulation | CD107a | ns | ns | 0.0095** | ns | ns | HD vs. FMS | 0.0390* |
| | | | | | | | HD vs. SpA | 0.0205* |

P values for the indicated antigens as a diagnostic indicator after all possible multiple comparisons between the groups (Kruskal-Wallis test), and after adjustment with the Dunn's multicomponent test (Adjusted P value) are shown. Group pairs showing a significant difference are also depicted (Adjusted P value).
ns: not significant.
total: total MAITs,
CD8+: CD8+ MAITs,
DN: DN MAITs.

Figure 4B:
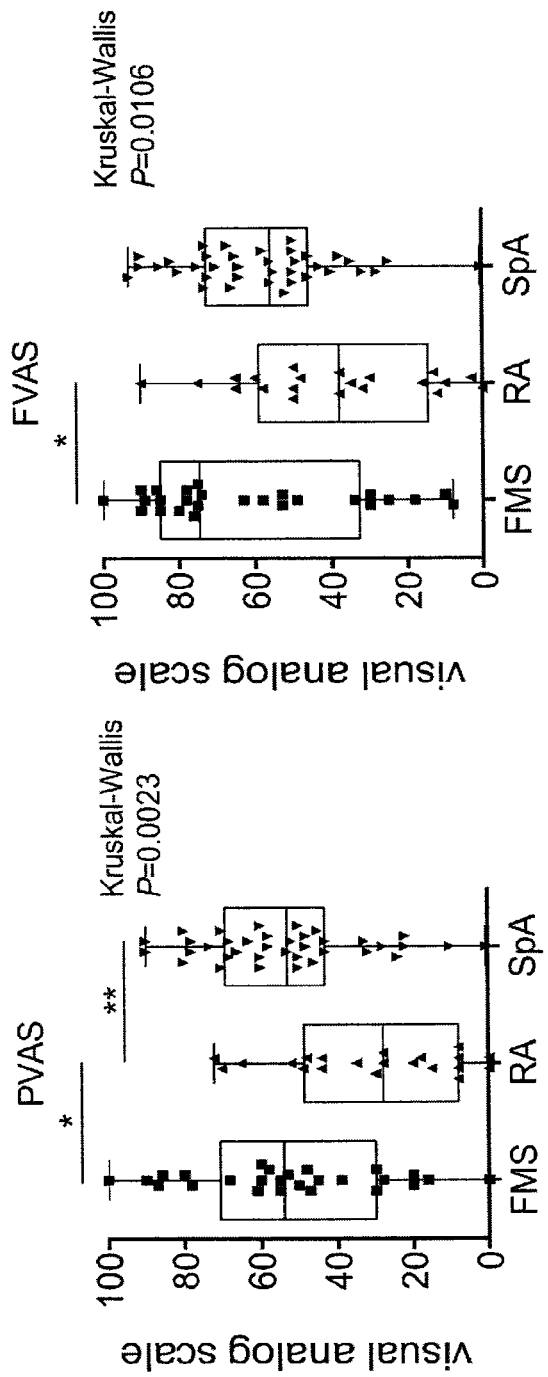
FIG. 4B shows the pain index, i.e., Pain Visual Analogue Scale (PVAS) in FMS, RA and SpA (left panel), and the fatigue index, i.e., Fatigue Visual Analogue Scale (FVAS) in FMS, RA and SpA (right panel).
Figure 4C:
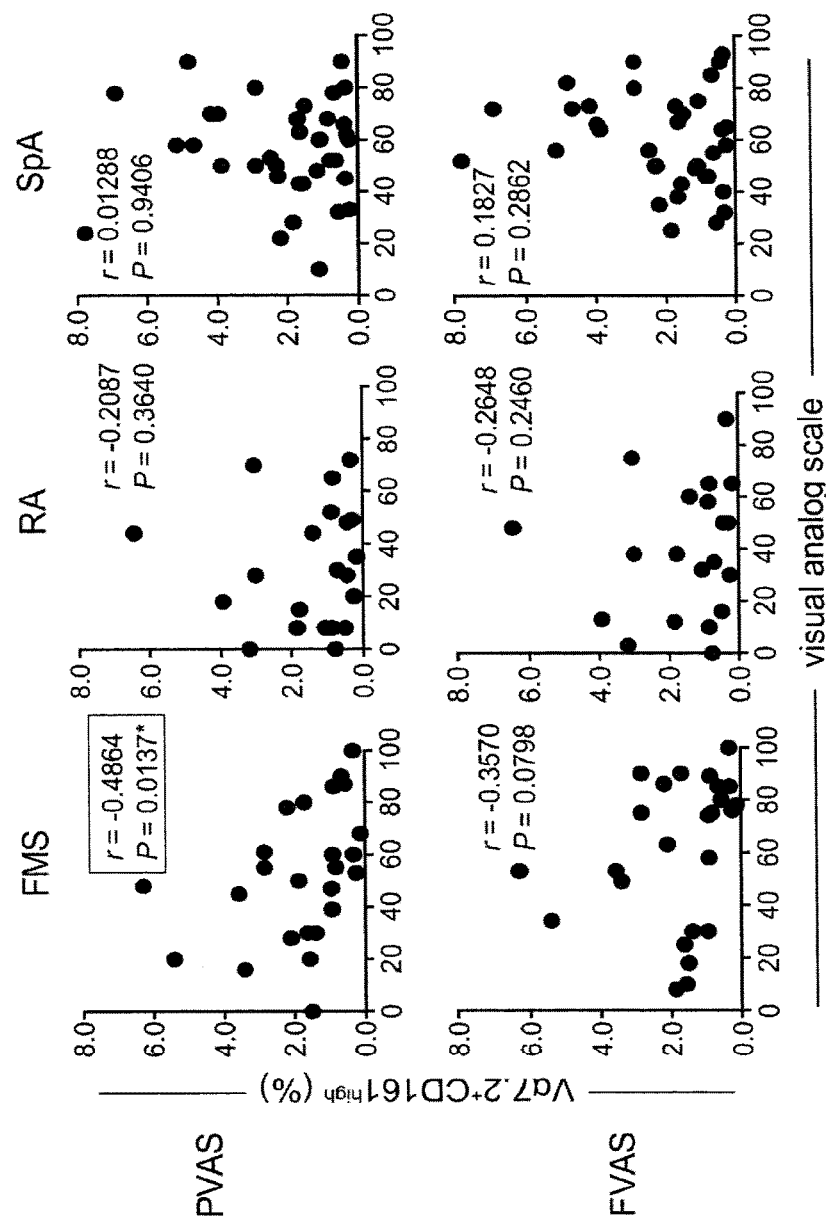
FIG. 4C shows correlation between PVAS/FVAS and MAIT cell percentage (% of Vα7.2$^+$CD161$^{high}$ cells among total CD3$^+$ cells in peripheral blood) in a cohort of 26 FMS (left panels), of 21 RA (middle panels), and of 36 SpA (right panels) patients. The correlation was analyzed with the Spearman rank correlation test. *: P<0.05, r: correlation coefficient.

Analysis of serum showed that RA had elevated levels of C-reactive protein (CRP) compared with FMS and/or SpA (FIG. 4A and Tables 7 and 8). Matrix metalloproteinase (MMP)-3 level in FMS was significantly lower than that in RA and SpA (FIG. 4A and Tables 7 and 8). Thus, CRP and MMP-3 might be potential biomarkers for distinguishing the diseases. Despite biomarkers such as CRP and rheumatoid factors, 20-50% of RA patients are devoid of them [Scott D L et al. (2010) Lancet 376: 1094-1108]. This means that there is a continuing need for a novel biomarker(s) for RA. In this respect, CCR7 may be a potential one for RA to distinguish from HD in total MAITs, and in CD8+ MAITs (FIGS. 3A-J, Tables 6A and B). When pain visual analog scale (PVAS) was compared, FMS and SpA showed a greater value than RA (FIG. 4B and Tables 7 and 8). Similarly, FMS exhibited a greater fatigue visual analog scale (FVAS) than RA (FIG. 4B and Tables 7 and 8). Intriguingly, there existed an inversed correlation between PVAS and the MAIT cell frequency in FMS, suggesting that MAITs would somehow be implicated in the pathology of FMS (FIG. 4C). Combined with data from the cell surface antigen analysis in MAITs, CRP, MMP-3, PVAS and FVAS may serve as auxiliary markers to distinguish FMS from RA and/or SpA.

TABLE 7

Statistics of the physical indexes (PVAS and FVAS), and of the biochemical indexes (CRP and MMP-3)

| clinical index | statistics | diseases FMS | RA | SpA |
|---|---|---|---|---|
| PVAS (score) | Numbers | 26 | 21 | 37 |
| | Minimum | 0.0 | 0.0 | 0.7 |
| | 25% Percentile | 30.0 | 8.0 | 43.0 |
| | Median | 54.0 | 28.0 | 53.0 |
| | 75% Percentile | 70.5 | 48.5 | 69.0 |
| | Maximum | 100.0 | 72.0 | 90.0 |
| FVAS (score) | Numbers | 26 | 21 | 37 |
| | Minimum | 8.0 | 0.0 | 0.6 |
| | 25% Percentile | 33.0 | 14.5 | 46.0 |
| | Median | 74.5 | 38.0 | 56.0 |
| | 75% Percentile | 85.0 | 59.0 | 72.5 |
| | Maximum | 100.0 | 90.0 | 93.0 |
| CRP (mg/L) | Numbers | 26 | 21 | 37 |
| | Minimum | 0.1 | 0.1 | 0.1 |
| | 25% Percentile | 0.1 | 0.3 | 0.1 |
| | Median | 0.2 | 1.5 | 0.2 |
| | 75% Percentile | 0.8 | 6.9 | 0.7 |
| | Maximum | 23.4 | 33.5 | 3.4 |

TABLE 7-continued

Statistics of the physical indexes (PVAS and FVAS), and of the biochemical indexes (CRP and MMP-3)

| clinical index | statistics | diseases FMS | RA | SpA |
|---|---|---|---|---|
| MMP-3 (ng/mL) | Numbers | 22 | 21 | 37 |
| | Minimum | 19.3 | 21.5 | 18.6 |
| | 25% Percentile | 25.3 | 46.4 | 36.0 |
| | Median | 29.6 | 71.8 | 47.7 |
| | 75% Percentile | 36.1 | 151.0 | 66.1 |
| | Maximum | 50.5 | 400.0 | 284.0 |

The number of subjects, and PVAS and FVAS score are shown. For CRP and MMP-3, serum concentration is indicated.

TABLE 8

P values for PVAS, FVAS, CRP, and MMP-3

| MAIT cell subset | P value (HD, FMS, RA, and SpA) | Adjusted P value | |
|---|---|---|---|
| PVAS | 0.0023** | FMS vs. RA | 0.0129* |
| | | RA vs. SpA | 0.0028** |
| FVAS | 0.0106* | FMS vs. RA | 0.0110* |
| CRP | 0.0011** | FMS vs. RA | 0.0079** |
| | | RA vs. SpA | 0.0014** |
| MMP-3 | <0.0001**** | FMS vs. RA | <0.0001**** |
| | | FMS vs. SpA | 0.0006*** |

P values are calculated with the Kruskal-Wallis test. The paired-groups exhibiting a statistical difference are shown with P values adjusted with the Dunn's multicomponent test (Adjusted P value).
Asterisk indicates significance.

Figure 5:
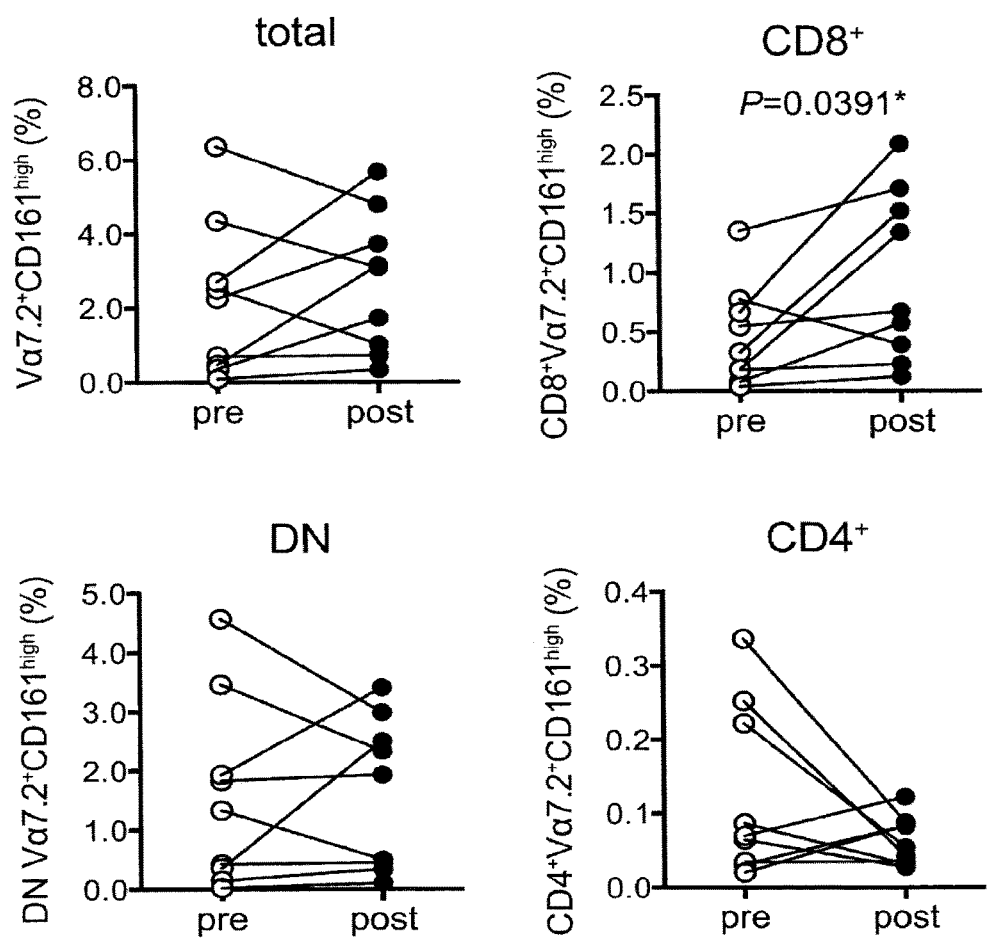
FIG. 5 shows the influence of the drug administration on MAIT cell frequency in FMS. The percentage of total, CD8$^+$, DN, and CD4$^+$ MAITs (Vα7.2$^+$CD161$^{high}$) within the total T cells (CD3$^+$) in peripheral blood from the same individuals (n=9) before and after the drug administration interruption is shown. The statistical significance and P value were calculated with the Wilcoxon matched-pairs signed rank test. Asterisk shows significance. *: P<0.05
Figure 6A:
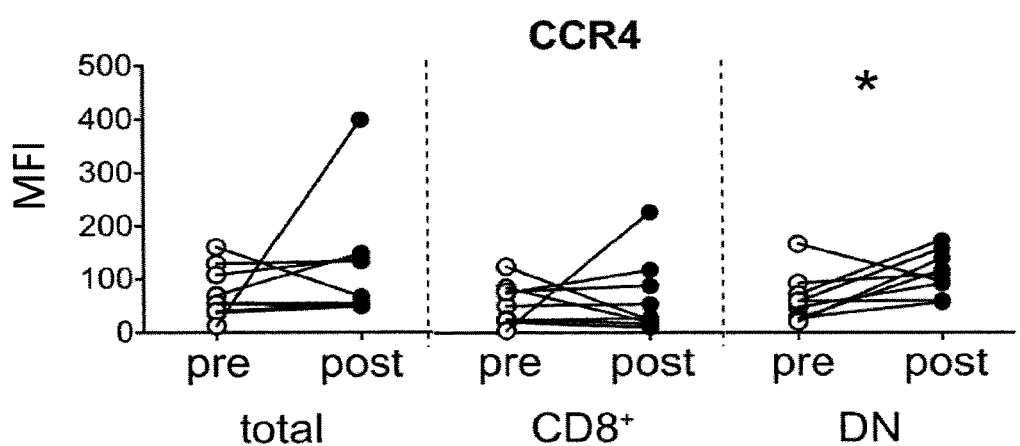
FIG. 6A shows influence of the drug administration on MAIT cell surface antigens (CCR4) in FMS. MFI of CCR4 in total, CD8$^+$, and DN MAITs in peripheral blood from the same individual (n=9) before and after the drug administration interruption is shown (the same applies to FIG. 6B-L). The statistical significance was assessed with the Wilcoxon matched-pairs signed rank test (the same applies to FIG. 6B-L). Asterisk shows significance (the same applies to FIG. 6B-L). *: P<0.05, **: P<0.01 (the same applies to FIG. 6B-L)
Figure 6B:
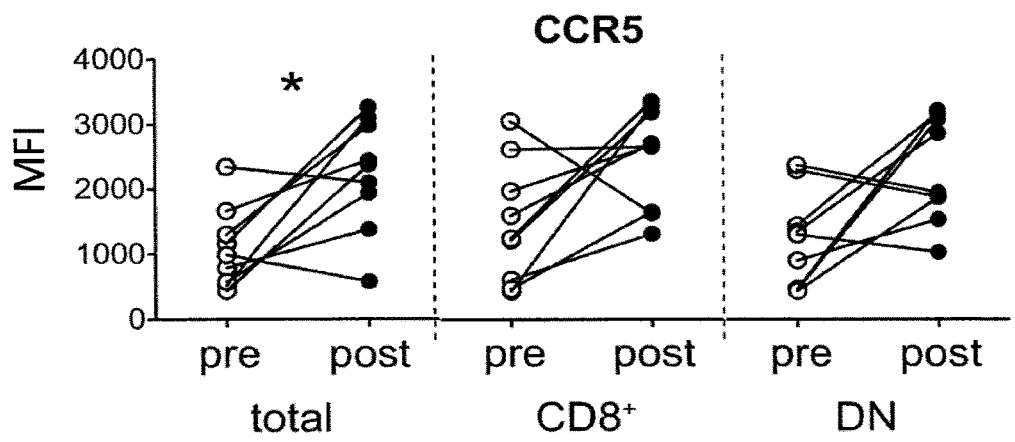
FIG. 6B shows influence of the daily drug administration on MAIT cell surface antigens (CCR5) in FMS.
Figure 6C:
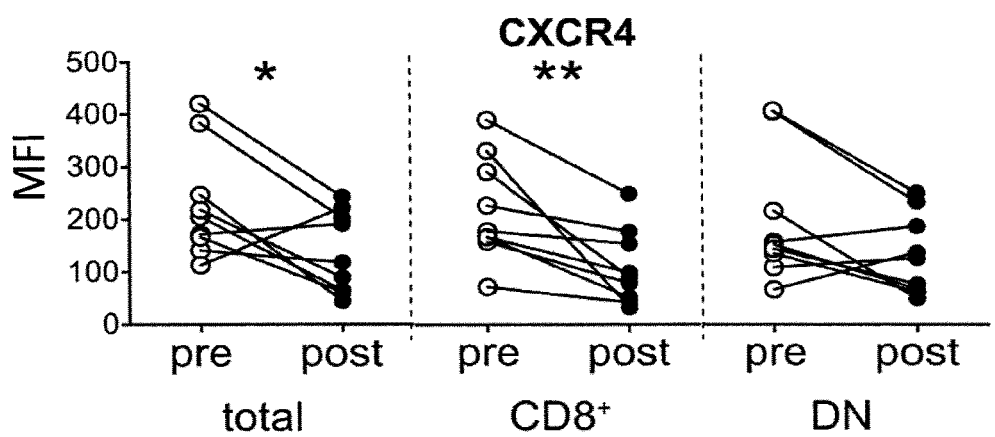
FIG. 6C shows influence of the daily drug administration on MAIT cell surface antigens (CXCR4) in FMS.
Figure 6D:
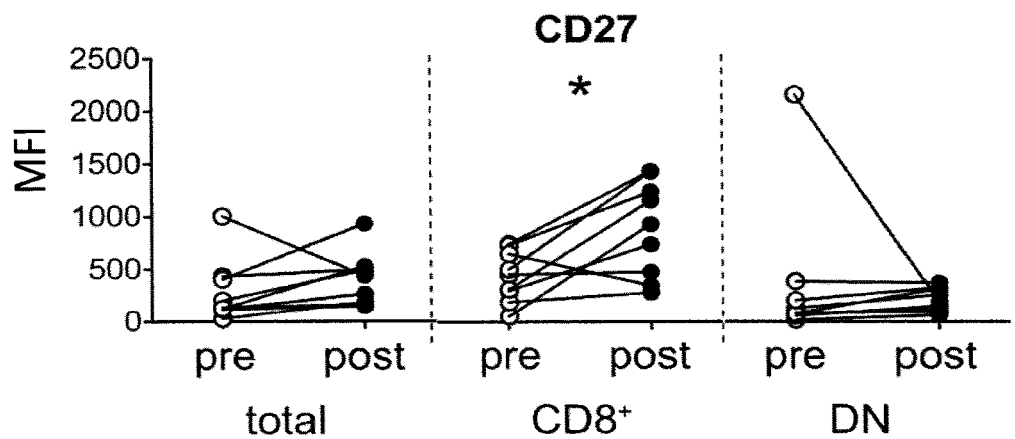
FIG. 6D shows influence of the daily drug administration on MAIT cell surface antigens (CD27) in FMS.
Figure 6E:
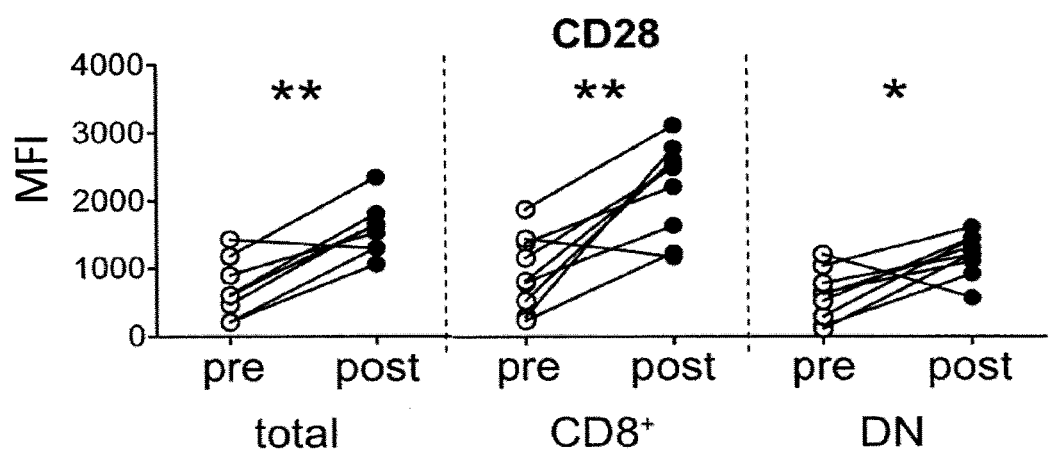
FIG. 6E shows influence of the daily drug administration on MAIT cell surface antigens (CD28) in FMS.
Figure 6F:
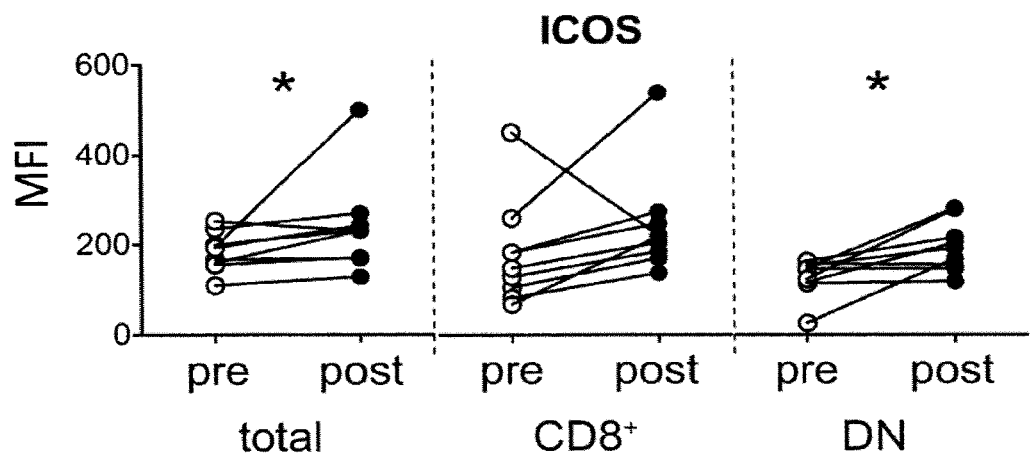
FIG. 6F shows influence of the daily drug administration on MAIT cell surface antigens (inducible costimulatory molecule (ICOS)) in FMS.
Figure 6G:
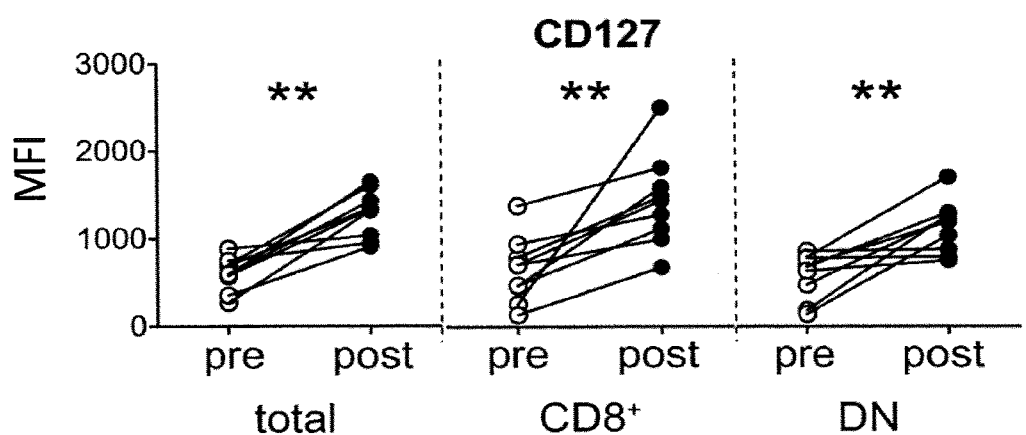
FIG. 6G shows influence of the daily drug administration on MAIT cell surface antigens (CD127) in FMS.
Figure 6H:
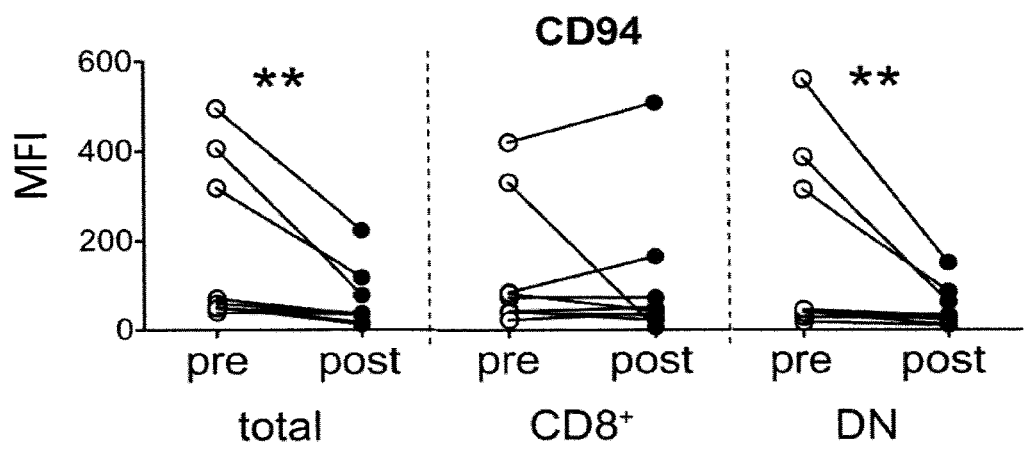
FIG. 6H shows influence of the daily drug administration on MAIT cell surface antigens (CD94) in FMS.
Figure 6I:
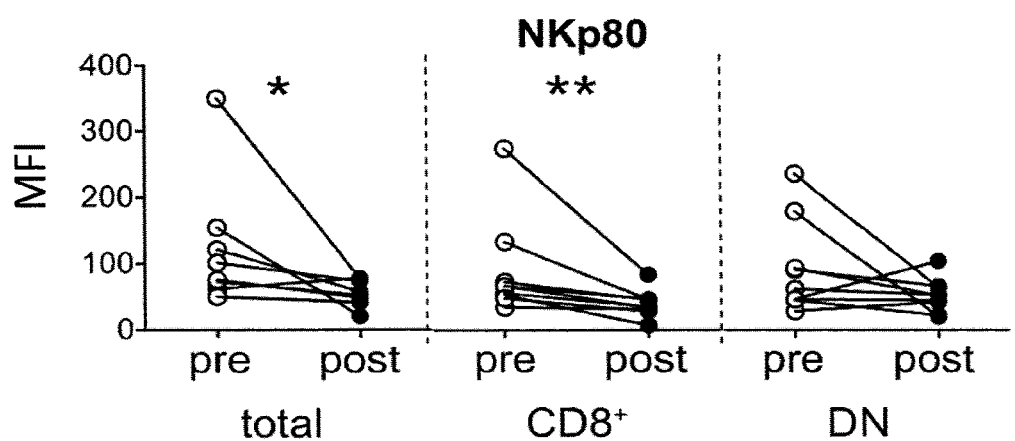
FIG. 6I shows influence of the daily drug administration on MAIT cell surface antigens (NKp80) in FMS.
Figure 6J:
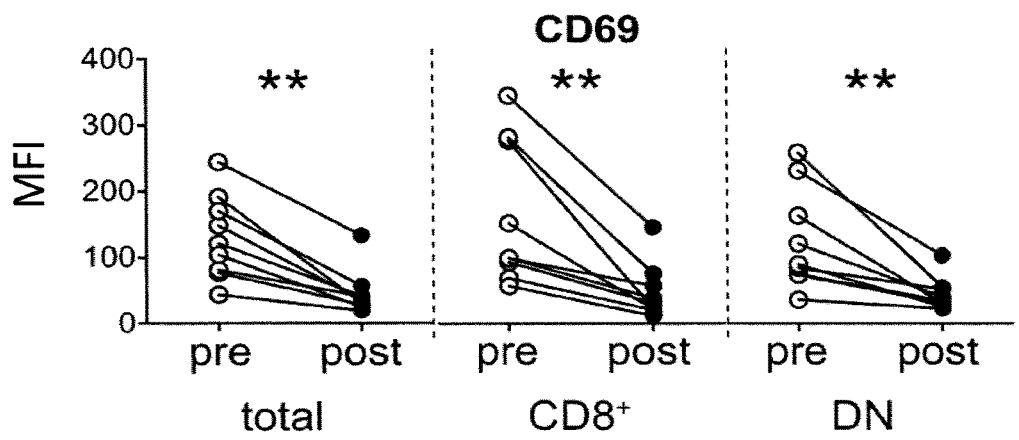
FIG. 6J shows influence of the daily drug administration on MAIT cell surface antigens (CD69) in FMS.
Figure 6K:
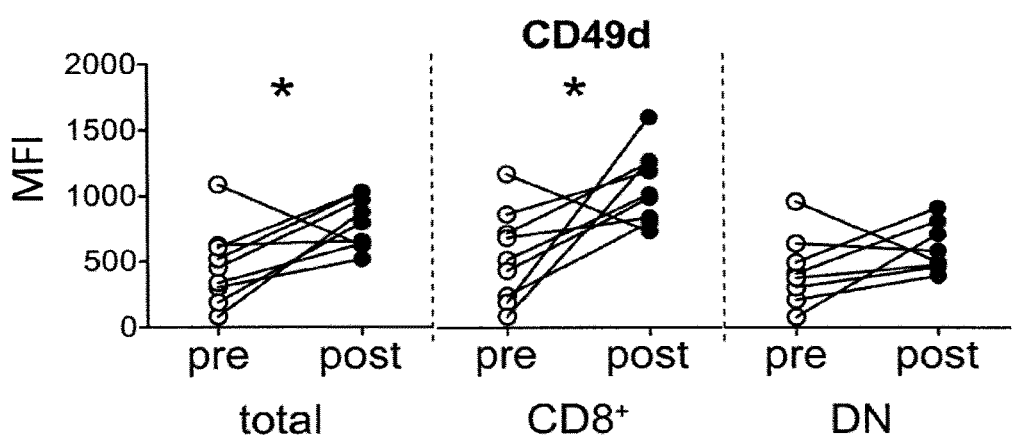
FIG. 6K shows influence of the daily drug administration on MAIT cell surface antigens (CD49d) in FMS.
Figure 6L:
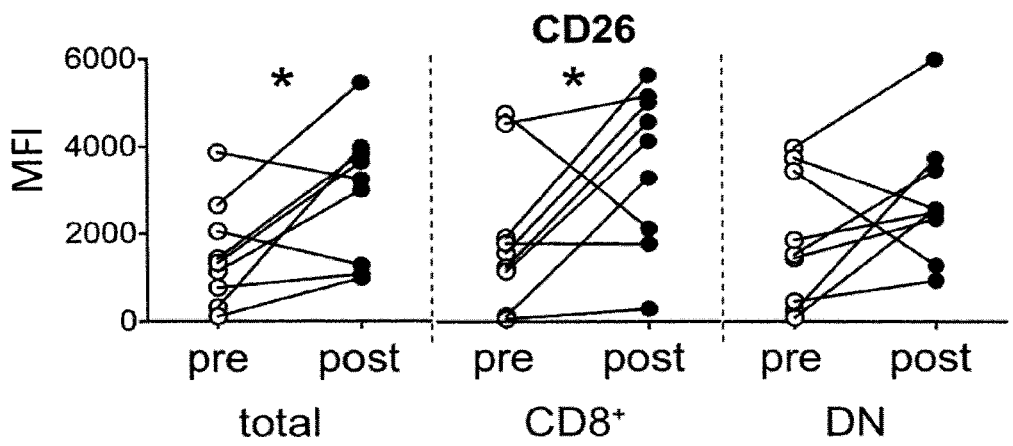
FIG. 6L shows influence of the daily drug administration on MAIT cell surface antigens (CD26) in FMS.

The present inventors then assessed whether the daily drug intake affected the frequency of MAIT cell subsets and the expression of the surface molecules in MAITs, as the FMS patients were ongoing treatment when the above analysis was performed (Table 9). After 48 h of the drug treatment interruption, CD8+ MAITs have increased in blood, while little change in CD4+, DN, and total MAIT cell frequency was observed, implying that CD8+ MAITs were sensitive to the drugs and would tightly be linked with the morbidity of FMS (FIG. 5 and Table 10). Such an interruption also engendered an increase of CCR4 in DN MAITs and of CCR5 in total MAITs, while CXCR4 expression has declined in total and CD8+ MAITs (FIG. 6A-L and Table 11). Given that CCR4 and CCR5 are receptors for the inflammatory chemokines such as CCL3, CCL3L1, CCL4, CCL5, CCL7, CCL8, and CCL11, such an increase indicated that the pathology of FMS comprises, in part, inflammation

[Kadetoff D et al. (2012) J Neuroimmunol 242: 33-38; and Sturgill J et al. (2014) J Immunol Res 2014: 938576]. Interruption of the drug treatment enhanced CD27 expression level in CD8+ MAITs (FIG. 6A-L and Table 11).

TABLE 9

Disease and medication history of the FMS patients analyzed in FIGS. 5 and 6

| Patient ID | Disease duration (years) | Duration of medication (years) | pharmacological treatment | | | | |
|---|---|---|---|---|---|---|---|
| | | | anti-depressant | anti-convulsant | opioid | steroid | NSAID |
| 1 | 6.0 | 1.7 | — | Pregabalin | Tramadol/Acetaminophen | — | — |
| 2 | 5.0 | 3.6 | Duloxetine | Pregabalin | Tramadol | — | — |
| 3 | 3.0 | 2.1 | — | Clonazepam | — | — | Naproxen |
| 4 | 5.0 | 3.8 | Duloxetine | Pregabalin Clonazepam | — | — | — |
| 5 | 5.0 | 4.7 | Duloxetine | Pregabalin | — | — | — |
| 6 | 11.0 | 2.8 | — | Clonazepam | — | — | — |
| 7 | 9.0 | 1.7 | — | Clonazepam | — | — | Aconite root powder |
| 8 | 3.0 | 2.2 | Duloxetine | — | — | — | — |
| 9 | 4.0 | 1.9 | Duloxetine | — | Tramadol | — | — |

NSAID: Non-steroidal anti-inflammatory drugs

TABLE 10

Statistics of the MAIT cell subset frequency before and after the drug treatment interruption in FMS

| Statistics | total | | CD4+ | | CD8+ | | DN | |
|---|---|---|---|---|---|---|---|---|
| | Pre | post | pre | post | pre | post | pre | post |
| P (Wilcoxon test) | 0.4961 | | 0.3594 | | 0.0391* | | 0.7344 | |
| Minimum | 0.1 | 0.3 | 0.0 | 0.0 | 0.0 | 0.1 | 0.0 | 0.1 |
| 25% Percentile | 0.4 | 0.9 | 0.0 | 0.0 | 0.1 | 0.3 | 0.3 | 0.4 |
| Median | 2.3 | 3.1 | 0.1 | 0.1 | 0.3 | 0.7 | 1.3 | 1.9 |
| 75% Percentile | 3.5 | 4.3 | 0.2 | 0.1 | 0.7 | 1.6 | 2.7 | 2.7 |
| Maximum | 6.4 | 5.7 | 0.3 | 0.1 | 1.4 | 2.1 | 4.6 | 3.4 |

The percentage of total, CD4+, CD8+, and DN MAITs (Vα7.2+CD161$^{high}$) within the total T cells (CD3+) from the same individuals (n = 9) before (pre) and after (post) the drug treatment interruption is shown.
P values are calculated with the Wilcoxon matched-pairs signed rank test.
Asterisk indicates significance.
*P < 0.05 total: total MAITs, CD4+: CD4+ MAITs, CD8+: CD8+ MAITs, DN: DN MAITs.

TABLE 11

P value calculated by statistics of the cell surface antigen MFI in total, CD8+, and DN MAITs before and after the drug treatment interruption in FMS

| Categories | antigens | P value | | |
|---|---|---|---|---|
| | | total | CD8+ | DN |
| chemokine receptors | CCR4 | 0.25 | >0.9999 | 0.0391* |
| | CCR5 | 0.0195* | 0.0547 | 0.0547 |
| | CXCR4 | 0.0391* | 0.0039** | 0.0742 |
| Costimulators | CD27 | 0.1289 | 0.0195* | 0.1641 |
| | CD28 | 0.0078** | 0.0078** | 0.0273* |
| | ICOS | 0.0273* | 0.0977 | 0.0156* |
| cytokine receptors | CD127 | 0.0039** | 0.0039** | 0.0039** |
| NK receptors | CD94 | 0.0039** | >0.9999 | 0.0039** |
| | NKp80 | 0.0195* | 0.0039** | 0.1641 |
| activation marker | CD69 | 0.0039** | 0.0039** | 0.0039** |
| integrin family | CD49d | 0.0391* | 0.0195* | 0.0977 |
| MAITs function-related molecule | CD26 | 0.0391* | 0.0391* | 0.2031 |

Cell surface antigens are categorized as shown above. MFI of the indicated cell surface antigen from the same individuals (n = 9) is omitted.
total: total MAITs, CD8+: CD8+ MAITs, DN: DN MAITs.
P values were calculated with the Wilcoxon matched-pairs signed rank test.
Asterisk indicates significance.
*P < 0.05,
**P < 0.01

Likewise, CD28 expression increased in all subset of MAITs (FIG. 6A-L and Table 11). Besides these, an increase of another costimulatory molecule ICOS was seen in total and DN MAITs (FIG. 6A-L and Table 11). CD127 expression was also augmented in all MAIT cell subsets (FIG. 6A-L and Table 11). These results suggested that MAITs in FMS possess an activated phenotype and that the elevated CD127 (IL-7 receptor alpha chain) expression would culminate in enhanced IL-17A and IFN-γ production [Pernambuco A P et al., (2013) Clin Exp Rheumatol 31: S60-S63; and Tang X Z et al. (2013) J Immunol 190: 3142-3152]. CD94 declined in total and DN MAITs, and also did NKp80 in total and CD8+ MAITs (FIG. 6A-L and Table 11). As HLA-E polymorphism associates with ankylosing spondylitis [Paladini F et al. (2009) Arthritis Res Ther 11: R171], the decrease in CD94 expression would result in an attenuated (CD94/NKG2A)-(HLA-E) interaction, which may be one of causal factors of FMS. The decrease of CD69 was also seen in all subset of MAITs (FIG. 6A-L and Table 11). This indicates that the drug treatment interruption kept MAITs being resting state. In contrast, CD49d, an integrin family member and CD26, a dipeptidase have increased in total and CD8+ MAITs (FIG. 6A-L and Table 11). Given that CD49d, the alpha 4 subunit of the very late antigen-4, is responsible for chronic lymphocytic leukemia cell homing to the bone marrow and to the lymphoid organs and that MAITs are found in the inflammatory lesions within the brain from multiple sclerosis patients [Brachtl G et al. (2014) Ann Hematol 93: 361-374; and Illés Z et al. (2004) Int Immunol 16: 223-230], it is predicted that MAITs altered the homing propensity through the molecule, and were closely related to the morbidity of FMS. The upregulated CD26 expression on MAITs after drug treatment interruption contrasted with what observed in $CD4^+$ T cells in RA where methotrexate treatment had little effect on CD26 expression [Ellingsen, T. et al Scandinavian Journal of Immunology, 66, 451-457 (2007)]. Since CD26 is responsible for truncation of precursors of many growth factors, chemokines, and cytokines, it is conceivable that such an increase of CD26 culminated in enhanced production of inflammatory mediators such as CCL11, IL-1, IL-6, and IL-8 in FMS [Rodriguez-Pintó I et al, (2014) Immunol Lett 161: 200-203; Bote M E et al. (2013) PLoS One 8: e74524; García J J et al. (2014) Ann Clin Biochem 51: 576-581; Imamura M et al. (2014) Clin Interv Aging 9: 939-944; and Ou X et al. (2013) Blood 122: 161-169]. Considering the enhanced production of other inflammatory cytokines as reported in FMS, these products would cause neuroendocrine anomaly, which eventually results in a widespread pain [Pernambuco A P et al., (2013) Clin Exp Rheumatol 31: S60-S63; Yunus M B (2012) Pain Res Treat 2012: 584573; and Sturgill J et al. (2014) J Immunol Res 2014: 938576]. In this regard, it may be speculated that MAITs which produce a plethora of inflammatory cytokines and chemokines are, at least in part, responsible for the pathology of FMS.

It is worthwhile to note that not all the antigens showing specific expression alternation in FMS have shown an alteration in expression upon drug treatment interruption. Indeed, the expression of CD150, CD244, CD8β, CCR7, and CD107a has not been affected (Tables 5 and 6A and B, and data not shown). These data in toto corroborates the fact that several cell surface molecules in MAITs serve as a diagnostic marker, and further indicated that they are susceptible to a variety of drugs such as anti-convulsant, anti-depressant, opioid, and non-steroidal anti-inflammatory drugs (Table 9, and FIGS. 5 and 6). Further study is warranted to decipher the molecular pathways and mechanisms for signaling between the drug intake and the phenotypic change in MAITs. Such an analysis would shed light on the function of MAITs in the etiology and/or pathology of FMS that has been remained conundrum.

The invention claimed is:

1. A method for detecting levels of mucosal associated invariant T cells (MAITs) or one or more surface antigens on MAITs, the method comprising
measuring (1) a frequency of MAITs relative to the total T cells in a sample, or (2) the expression level of one or more surface antigens on MAITs selected from the group consisting of CD4, CD8, CCR4, CCR7, CXCR1, NKp80, CD150, CD107a, CD8β, CD44 and CXCR4 in a sample, wherein said sample is a biological sample collected from a human having fibromyalgia syndrome or suspected of having fibromyalgia syndrome.

2. The method according to claim 1, wherein said surface antigens are selected from the group consisting of CD4, CCR4, CCR7, CSCR1, NKp80, CD150, CD107a and CD8β.

3. The method according to claim 1, wherein the expression level of one or more surface antigens selected from the group consisting of CCR7, NKp80, CD150 and CD8β on CD8 positive ($CD8^-$) cells in said MAITs is measured.

4. The method according to claim 1, wherein the expression level of one or more surface antigens selected from the group consisting of CCR4, CXCR1 and CD107a on CD4 and CD8 double negative ($CD4^-CD8^-$) cells in said MAITs is measured.

5. The method according to claim 1, wherein said surface antigen is CD44 or CXCR1 or both CD44 and CXCR1.

6. The method according to claim 1, wherein the expression level of CXCR1 on the $CD4^-CD8^-$ cells in said MAITs is measured.

7. The method according to claim 1, wherein the surface antigen is CXCR4.

8. The method according to claim 1, wherein the sample is peripheral blood.

9. The method according to claim 1, wherein the expression level is a protein amount.

10. The method according to claim 9, wherein the protein amount is measured with an antibody against the one or more surface antigens.

11. The method of claim 1, comprising detecting the expression level of CD150 and at least one of (A) CD44, CXCR1, or both; (B) CRP, MMP-3, PVAS, FVAS, or a combination thereof.

12. A method for treating fibromyalgia syndrome (FMS) in a subject in need thereof, the method comprising administering an effective amount of a drug to the subject to treat FMS, wherein said drug is selected from the group consisting of methotrexate, sulfasalazine, a corticosteroid, an anti-convulsant, an anti-depressant, an opiate and neurotrophin, wherein the subject has been identified as a subject in need thereof by diagnosing FMS by using measured value(s) of surface expression level of CD150 on mucosal associated invariant T cells (MAITs) in a sample, and (1) a frequency of MAITs relative to the total T cells in a sample, or (2) the expression level of one or more surface antigens on MAITs selected from the group consisting of CD4, CD8, CCR4, CCR7, CXCRI, NKp80, CD107a, CD83, CD44 and CXCR4 in a sample, wherein said sample is a biological sample collected from a human.

13. The method of claim 12, wherein the diagnosing further comprises differentiating an FMS subject from a healthy subject.

* * * * *